United States Patent
Murphy et al.

(10) Patent No.: US 11,194,888 B1
(45) Date of Patent: Dec. 7, 2021

(54) SYSTEM FOR UBIQUITOUS DETECTION AND MONITORING OF SYMPTOMS OF PARKINSON'S DISEASE

(71) Applicant: Verily Life Sciences LLC, Mountain View, CA (US)

(72) Inventors: Mark Murphy, Mountain View, CA (US); Erin Soderberg, San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 228 days.

(21) Appl. No.: 15/481,510

(22) Filed: Apr. 7, 2017

(51) Int. Cl.
*G06F 19/00* (2018.01)
*G16H 40/63* (2018.01)

(52) U.S. Cl.
CPC ...... *G06F 19/3481* (2013.01); *G06F 19/3418* (2013.01); *G16H 40/63* (2018.01)

(58) Field of Classification Search
CPC .. G06F 19/3481; G06F 19/3418; G16H 40/63
USPC .......................................................... 705/2
See application file for complete search history.

(56) References Cited

U.S. PATENT DOCUMENTS

2015/0164377 A1* 6/2015 Nathan ................ A61B 5/1122
600/595

FOREIGN PATENT DOCUMENTS

WO    WO-2013012625 A1 * 1/2013    ......... A61N 1/36067

OTHER PUBLICATIONS

Oung, Qi Wei et al. "Technologies for Assessment of Motor Disorders in Parkinson's Disease: A Review." Sensors (Basel, Switzerland) vol. 15,9 21710-45. Aug. 31, 2015, doi:10.3390/s150921710 (Year: 2015).*
Tzallas et al., "Perform: A System for Monitoring, Assessment and Management of Patients with Parkinson's Disease", Sensors 2014, 14, 21329-21357.
El-Gohary et al., "Continuous Monitoring of Turning in Patients with Movement Disability", Sensors 2014, 14, 356-369.
Curtze et al., "Prescribed gait tests versus continuous monitoring of gait in people with Parkinson's disease".
Taylor, "Roche rolls out smartphones for continuous monitoring of participants in Parkinson's trial", Aug. 17, 2015.

* cited by examiner

*Primary Examiner* — Jonathan Ng
*Assistant Examiner* — Christopher B Wehrly
(74) *Attorney, Agent, or Firm* — McDonnell Boehnen Hulbert & Berghoff LLP

(57) ABSTRACT

A system is provided to monitor, over time, one or more physical variables related to a severity or progression of a movement disorder and/or of symptoms thereof. The monitored physical variables can include speech sounds; keyboard outputs; or accelerations, rotations, or other properties of the motion of one or more body parts. The system operates to detect, based on the monitored one or more physical variables, potential changes in the degree and/or character of the movement disorder symptoms. In response to detecting such a potential change, the system provides the user with one or more tasks that the user can perform. The system detects one or more properties of the user's performance and, based on that detection, determines the severity or progression of the movement disorder. The tasks can include stepping, turning, standing, sitting, reaching, typing, pointing, manipulating an object, speaking into a microphone, or other tasks.

19 Claims, 9 Drawing Sheets

US 11,194,888 B1

SYSTEM FOR UBIQUITOUS DETECTION AND MONITORING OF SYMPTOMS OF PARKINSON'S DISEASE

BACKGROUND

The health or physical state of a person, or a type or degree of a disease state or process, may correlate with a variety of properties or processes of the person's body. These properties or processes may be detected and used to determine such health or disease information. For example, an amount, frequency, or other characteristics of tremor in voluntary or involuntary muscle forces produced by a person may be related to the presence or type of locomotor disease or syndrome suffered by the person (e.g., Parkinson's disease, multiple sclerosis), related to a degree or severity of the disease (e.g., to a rating on a clinical scale of disease severity/progression), and/or related to an efficacy of a treatment for the disease (e.g., to a timing of administration, dosage, or other property of a pharmaceutical treatment). Additionally or alternatively, changes in such properties or processes may be related to changes or progression of such a disease or other health state. Measured properties or processes from a particular person may be compared to population norms and/or to previously measured information from the particular person in order to diagnose a disease, determine a disease state or progression, or determine some other health information about the particular person.

Properties or processes related to a health state may be measured in a clinical setting, e.g., by a doctor or other medical professional using systems or devices (e.g., load cells, balance boards, goniometers) present in a clinical setting. Additionally or alternatively, such properties or processes may be measured in the home in order to reduce costs, increase convenience, permit a higher frequency of measurement, or to provide some other benefit.

SUMMARY

Some embodiments of the present disclosure provide a system that includes: (i) a first sensor that monitors motion of a person; (ii) a second sensor that monitors performance of a motor task; (iii) a user interface; and (iv) a controller communicatively coupled to the first sensor, the second sensor, and the user interface. The controller includes a computing device programmed to perform operations including: (a) detecting, using the first sensor during a first period of time, a first signal relating to motor activity of the person; (b) obtaining a baseline activity profile based on the first signal; (c) detecting, using the first sensor during a second period of time, a second signal relating to motor activity of the person; (d) determining, based on the second signal and the baseline activity profile, that the motor activity of the person during the second period of time differs from the baseline activity profile; (e) responsive to determining that the motor activity of the person during the second period of time differs from the baseline activity profile, using the user interface to provide a prompt to perform a motor task; and (f) after using the user interface to provide the prompt, using the second sensor to detect a third signal related to the motor task.

Some embodiments of the present disclosure provide a non-transitory computer-readable medium having stored thereon instructions executable by at least one processor to perform operations. The operations include: (i) detecting, using a first sensor during a first period of time, a first signal relating to motor activity of a person; (ii) obtaining a baseline activity profile based on the first signal; (iii) detecting, using the first sensor during a second period of time, a second signal relating to motor activity of the person; (iv) determining, based on the second signal and the baseline activity profile, that the motor activity of the person during the second period of time differs from the baseline activity profile; (v) responsive to determining that the motor activity of the person during the second period of time differs from the baseline activity profile, using a user interface to provide a prompt to perform a motor task; and (iv) after using the user interface to provide the prompt, using a second sensor to detect a third signal related to the motor task.

These as well as other aspects, advantages, and alternatives, will become apparent to those of ordinary skill in the art by reading the following detailed description, with reference where appropriate to the accompanying drawings.

DETAILED DESCRIPTION

Figure 1A:
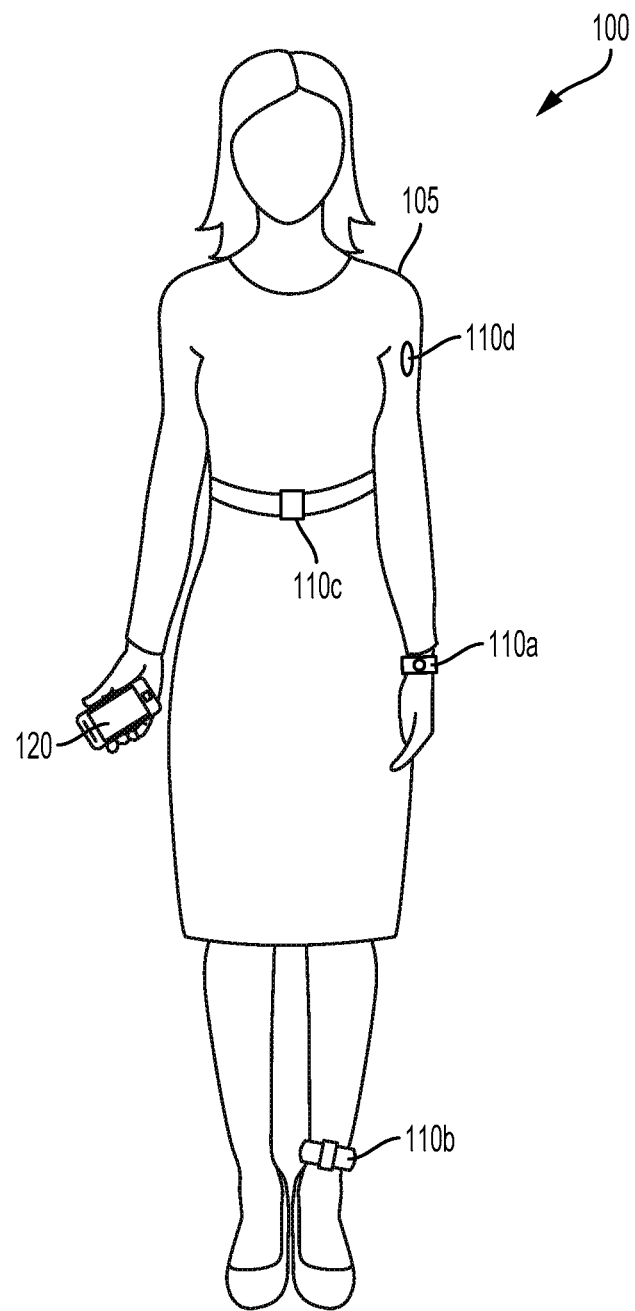
FIG. 1A illustrates body-mountable devices of an example system being worn by a wearer.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

The presence, progression, type, degree, or other properties of a disease state or process may be detected in a clinical setting by measuring one or more correlates of the disease state or process. Such correlates can include properties of body motion during a specified task (e.g., a tremor during a fine motor control task, a speed or coordination of motion during treadmill walking), properties of the cardiovascular system or other body systems at rest or in response to some specified task or activity (e.g., a heart rate or pulse timing variability at rest or during strenuous exercise), or some other measured properties. However, limiting the detection of many clinically relevant properties to a clinical environment (e.g., a doctor's office, a rehab clinic) may result in a very limited amount of disease or other health information about a person. Further, such information may be expensive to generate in terms of both medical spending and time to travel to the clinical environment and to undergo measurements. It could be beneficial to provide devices and systems to detect properties of clinical relevance outside of the clinical environment (e.g., in the home, at a person's place of work) in order to reduce the cost of such information, to increase the amount of information generated and/or to increase a temporal resolution of such information, or to provide other benefits.

A person could perform one or more specified diagnostic tasks at home in order to provide more accurate, higher resolution, or otherwise higher quality information about a disease state or process. Such diagnostic tasks could include motor tasks corresponding to activities of daily living (e.g., manipulating a utensil, locomoting, standing or sitting, typing on a keyboard or touchscreen, speaking), motor tasks corresponding to elements of a clinically-relevant medical test or battery (e.g., motor tasks corresponding to some or all of the elements of the unified Parkinson's disease rating scale (UPDRS) or the multiple sclerosis functional composite (MSFC)), motor tasks that approximate or are otherwise related to elements of a clinically-relevant medical test or battery, or some other structured tasks.

Such a task could be performed at a specified time of day, at a specified time relative to an activity (e.g., eating, walking, taking a medication), or according to some other specified schedule or timing. However, such tasks could require an amount of effort or time that reduces compliance with the task and/or that affects the quality of performance of the task by the person. For such tasks, it could be beneficial to prompt a person to perform the task when such performance would be especially beneficial, e.g., during the occurrence of a particular symptom (e.g., a rare disease-related event), when a particular symptom or an overall disease severity changes (e.g., increases or decreases), when a symptom that is potentially related to the disease state or process changes, or at some other time when information detected about the disease state or process may be especially diagnostically relevant.

A device or system of devices (e.g., a cell phone, a watch, a wearable health device) could operate to detect signals relevant to the disease state or process (e.g., to detect accelerations or rotations related to tremor, locomotion, or other motor activity that may have properties related to the disease state or process) over a protracted period of time (e.g., during most of the day). These detected signals could be used to detect a change in a symptom of the disease state or process or to detect some other property of a person's physiological and/or behavioral state. The device or system of devices could then, responsive to detecting such a change in symptom level or severity or other property, prompt the person to perform one or more motor tasks. Such motor tasks could be performed using and/or assessed by some separate device or system (e.g., a keyboard of a computer, an EMG detection system or other clinical assessment apparatus). Additionally or alternatively, the device or system of devices used to detect that the person should be prompted to perform a diagnostic motor task may also operate to detect the person's performance of the motor task (e.g., by operating an accelerometer to determine the speed of motion of the person while locomoting) and/or to provide feedback or other information to the person during performance of the motor task (e.g., by operating a touch screen display to provide a set of typing or other interface-manipulation tasks that the person could perform).

A variety of wearable or otherwise body-mountable devices could be provided to measure a variety of different physical variables of a person and/or to facilitate performance and assessment of specific motor tasks. The devices could be worn throughout the day and/or at night to provide more clinically-relevant data, and this data can be accessed across a broader range of activities (e.g., normal walking, food preparation, engaging in other activities of daily living), times of day, or other potentially relevant conditions. A system as described herein could include multiple different devices mounted to respective different body segments, e.g., to detect properties of the different body segments. For example, a system could include devices mounted to an ankle, torso, head, or other body segment(s) of a person. Each such body-mountable device could include a single sensor (e.g., an accelerometer, a gyroscope, a temperature sensor, a photoplethysmographic sensor, an EMG sensor) or multiple sensors.

Such a system could include a controller to receive information about the body from the different body-mountable devices and/or sensors thereof. The controller could be included in one of the body-mountable devices (e.g., in a device configured to be mounted to the wrist and to provide a user interface or other functionality in addition to one or more sensors for detecting properties of the wrist). Additionally or alternatively, such a controller could be part of a cell phone or other device. The different body-mountable device and/or the controller could be in wireless communication (e.g., the body-mountable device(s) could send indications of measured properties via Bluetooth to a cell phone or other device that includes the controller), connected via cables, or communicatively or otherwise coupled in some other way.

Additionally or alternatively, a system as described herein could be implemented in a cell phone without including additional sensors or devices. For example, an inertial measurement unit of a cell phone could operate to detect a mean step duration, a mean turn velocity, a percent of the day occupied by locomotion or other active tasks, or some other properties that may be related to a disease state or process of a person. The cell phone could then determine whether such detected properties have changed or have some other property indicating that a diagnostic motor task should be performed. Responsive to such a determination, the cell phone could prompt the person to perform a motor task (e.g., to speak into the phone, to press one or more button or other user interface elements on a touch screen of the cell phone) and could operate one or more sensors (e.g., a microphone, a touch sensor of a touch screen) to detect a signal related to performance of the prompted motor task.

Further, the controller and/or the body-mountable devices could be in communication with a remote server, cloud computing service, or other remote systems. Such communications could include the controller and/or body-mountable devices providing information to the remote system, e.g., signals detected from a person's body, determined characteristics of events (e.g., footsteps, heartbeats) that are present in such signals, signals related to the performance of prompted motor tasks, or other information. Additionally or alternatively, the controller and/or body-mountable devices could receive information from the remote system, e.g., updates or epidemiological information, predictive models, diagnoses or other information determined based on information sent to the remote system, or other information. The controller and/or body-mountable devices could log detected or determined information and upload such information at discrete points in time and/or controller and/or body-mountable devices could continuously upload data.

It should be understood that the above embodiments, and other embodiments described herein, are provided for explanatory purposes, and are not intended to be limiting.

II. EXAMPLE SYSTEM OF BODY-MOUNTABLE DEVICES

Sensors disposed in one or more body-mounted or otherwise configured devices can generate signals related to the health, disease state, or other properties of a person (e.g., of a wearer of a body-mounted device). By wearing or otherwise interacting with these devices (e.g., by placing a cell phone in a pocket) for a protracted period of time and/or while performing or otherwise engaging in a variety of different activities, the signals generated by such a system (e.g., of multiple body-mountable devices) could be used to determine such properties of the person's body or activities. For example, such information could be used to diagnose a disease, to determine that such a disease has progressed, to determine an efficacy or dose of a drug or treatment, to predict that a particular health event (e.g., a heart attack, an incident of arrhythmia) is likely to occur, to determine the timing of a particular event (e.g., the onset or contraction of a disease), to determine the efficacy of an exercise, to determine whether a person is engaging in an activity correctly (e.g., performing exercise without unduly risking injury), or to determine some other information about the person's body.

Further, such a system could prompt the person to engage in one or more diagnostic motor tasks (e.g., standing, sitting, typing, talking or other activities of daily living) to generate further information about the person's physiological or behavioral state. For example, the system could detect one or more signals related to the person's performance of the prompted motor task. Such task-related signals could include an acceleration or rotation related to locomotion or other movements, one or more button outputs related to use of a keyboard, sound related to speech, a pressure signals or other signals related to interaction with a touch screen, or some other signals related to performance of the task.

FIG. 1A illustrates an example system 100 for detecting a variety of signals related to a wearer 105, e.g., related to one or more body segments of the wearer 105. The system 100 includes a number of body-mountable devices 110a, 110b, 110c, 110d and a cell phone 120. The arrangement, number, location, and other properties of the system 100, and of the body-mountable devices or other elements thereof, are intended as a non-limiting example embodiment. A system as described herein could include more or fewer body-mountable devices or other elements (e.g., could lack a cell phone, could include a base station, control pendant, or other non-body-mounted elements), could consist only of non-body-mountable devices (e.g., could consist only of the cell phone 120), or could be configured in some other way.

Each of the body-mountable devices 110a-d of the system 100 includes at least one sensor that monitors motion of a person. Such a sensor could be configured to generate a signal related to motor activity of the wearer 105, e.g., to a motion, rotation, acceleration, pulse rate or other cardiovascular property, exerted force or pressure, or other properties of the body part to which the body-mountable device is mounted. In some examples, such a sensor could include a camera (e.g., a camera of the cell phone 120 or of some other device that is facing the wearer 105) that could be operated to generate one or more images depicting motion of the wearer 105, performance of a motor task by the wearer 105 (e.g., a motor task which the system 100 prompted the wearer 105 to perform), or depicting some other information about the wearer 105. The cell phone 120 may additionally or alternatively include one or more sensors configured to generate such a signal.

Each component device (e.g., each of the body-mountable devices 110a-d and/or the cell phone 120) of the system could have the same sensor(s) or different sensors. A particular body-mountable device 110a-d could be securely mounted to a body segment (e.g., by being strapped, adhered using an adhesive, included in a tight-fitting garment, or otherwise secured to the body segment) of the wearer 105. Alternatively, a particular body-mountable device 110a-d or other component of the system 100 (e.g., the cell phone 120) could be loosely mounted to a body segment of the wearer 105 (e.g., by being included in a loose-fitting garment, by being draped around a part of the wearer's 105 body, being placed in the wearer's hand or in a pocket of a garment worn by the wearer) or otherwise loosely related to the body of the wearer 105 such that the particular component of the system 100 can monitor motion of the wearer 105 and/or to monitor performance of a motor task by the wearer 105 (e.g., performance of a motor task performed by the wearer 105 in response to receiving a prompt to perform such a motor task).

The sensors of the system (e.g., of the body-mountable devices 110a-d and/or cell phone 120) could include accelerometers, gyroscopes, pressure sensors, strain sensors, magnetometers, global positioning system (GPS) receivers, photoplethysmographic sensors, laser speckle flowmeters, tonometers, blood pressure cuffs, electrocardiogram (ECG) electrodes, electromyogram (EMG) electrodes, galvanic skin resistance electrodes, thermometers, galvanic skin potential electrodes, ambient light sensors, cameras, touch screens and/or touch sensors of touch screen, user interface elements (e.g., buttons), microphones, or some other sensors or other elements. The sensors of the body-mountable devices 110a-d could be configured to generate signals related to motion (e.g., acceleration, velocity, rotation) or location (e.g., absolute location, location relative to another body segment, orientation relative to gravity) of a body segment, the temperature of a body segment, hemodynamic properties of blood and/or vasculature of the body segment (e.g., a blood flow rate, a pulse rate, a pulse timing, a pulse transit time, a blood oxygenation percent), an image of the wearer 105 and/or portions of the wearer's 105 body, an angle of a joint, a force exerted on the body segment (e.g., from an object, from the ground), an ambient light or temperature in the environment of the body segment, or some other properties of a body segment and/or its environment.

Body-mountable devices 110a-d, the cell phone 120, or other elements (e.g., a data logger, a controller, a communications bridge) of the system 110 could be in wired or wireless communication or otherwise communicatively coupled. For example, components of the system 100 could communicate via an ad-hoc wireless network standard (e.g., ZigBee). Additionally or alternatively, one or more devices of the system 100 could operate as a master, wirelessly transmitting commands to other devices of the system 100 and/or receiving information (e.g., wireless indications of signals generated by sensors of the system 100) from the other devices. In examples wherein one or more devices of the system 100 are in wired communication, power could also be provided between the devices of the system, e.g., a particular one of the devices could include a battery or other power source that could provide power to the particular one of the devices in addition to any devices in wired communication therewith.

The system 100 includes a controller that is communicatively coupled to the sensors and that can operate to receive the signals generated by the sensors of the system 100, to perform operations related to such signals, to provide prompts or other indications to the wearer 105 (e.g., prompts to perform one or more specified motor tasks), to receive sensor signals related to performance of such motor tasks, and/or to facilitate some additional operations of the system 100.

For example, the controller could, based on user inputs, sensor signals, or other information, determine or otherwise obtain (e.g., by receiving information from a server or other remote system) a baseline activity profile based on the wearer's 105 motor activities (as detected by sensors of the system 100) during one or more periods of time (e.g., during one or more days, weeks, or other time periods). Such a baseline activity profile could describe properties of discrete events (e.g., sensor data or patterns of sensor outputs recorded during such events) or other motor activity of the wearer 105. For example, a baseline activity profile could represent a mean, range, standard deviation, or other information about a sample of footstep durations, discrete turns during locomotion, a fraction or percentage of time (e.g., of each day, of each hour) that the wearer 105 engages in locomotion or in some other specified motor activity, velocity of individual bouts of locomotion, or a sample of some other discrete motor activities. The controller could determine such a baseline activity profile itself (e.g., by performing an analysis on sensor signals stored in a memory accessible by the controller) or could transmit indications of sensor signals to a remote system (e.g., to a cloud computing environment, via a cellular data link) and subsequently receive an indication, from the remote system, of a baseline activity profile determined by the remote system based on the transmitted sensor signals.

The controller could, after obtaining a baseline activity profile that is based on or otherwise related to the wearer's 105 motor activities during a period of time (e.g., during a period of hours, days, or weeks prior to a particular point in time), detect further sensor signals related to the wearer's 105 motor activities. Additionally or alternatively, such additional signals could also be used to determine the baseline activity profile. The controller could use such signals to determine whether to prompt the wearer 105 to perform a diagnostic motor task. This could include using the detected signals to determine that the motor activity of the wearer differs in some way from the baseline activity profile. For example, the controller could determine a property of a number of discrete events within the wearer's 105 motor activity (e.g., a duration of a number of steps taken by the wearer 105 while walking) and could determine that a mean, a standard deviation, a range, or some other property or properties of a distribution of the determined properties differs from the baseline activity profile. Responsive to determining that the wearer's 105 motor activity differs from the baseline activity profile in such a way, the controller could operate one or more components of the system (e.g., a speaker or screen of the cell phone 120, a beeper or buzzer of the wrist-mounted device 110a) to prompt the wearer 105 to perform a specified motor task. The controller could additionally operate one or more sensors of the system 100 that are configured to monitor performance of the motor task to detect a signal related to the wearer's 105 performance of the prompted motor task.

The controller could determine an activity being performed or otherwise engaged in by the wearer 105 (e.g., resting, sleeping, walking, running, locomoting). The controller could detect discrete events that are taking place (e.g., footsteps, body motions, periods of rapid eye movement (REM) sleep) and/or determine characteristics of such events (e.g., the duration of a period of REM sleep, the duration of the stance phase of a footstep, the duration of a continuous period of locomotion).

The controller could transmit sensor signals or other information to a remote system (e.g., a server, a cloud computing service) and/or transmit information determined from the sensor signals (e.g., an activity of the wearer 105 at a particular point in time, signals related to the performance of a prompted motor task, detected events and/or determined characteristics thereof detected from the sensor signals, health state information determined from the sensor signals, event characteristics, and/or performance of one or more prompted motor tasks). The controller could additionally or alternatively transmit indications of such information to a wearer or other user (e.g., a physician) via an audio or video user interface element (e.g., a histogram or other visual indication of a sample of determined characteristics of a particular event detected during a particular activity, an audio or visual indication of a determined disease severity level or other determined health state).

Such a controller of the system 100 could be disposed in one of the body-mountable devices, e.g., in a wrist-mountable device 110a that may include a display, buttons, a touchscreen, or some other user interface elements. Additionally or alternatively, such a controller could be disposed in the cell phone 120 or in some other element or device of the system 100. In such an example, the cell phone 120 or other controller-bearing element of the system 100 could, itself, include one or more sensors (e.g., accelerometers, gyroscopes, GPS receivers) that could be operated to generate signals related to the wearer's 105 body, activities, performance of a prompted motor task, or environment or related to some other properties of interest. The controller of the system 100 could be implemented as a special-purpose computing device (e.g., a microcontroller of a discrete control pendant or other device). Additionally or alternatively, elements of the controller could be implemented by a general-purpose computing device, e.g., a microprocessor of the cell phone 120. In such an example, functionality of the controller could be provided by instructions stored in a computer-readable medium (e.g., a flash memory of the cell phone 120) that could be executed by the controller. Such instructions could be provided in the form of an application that could be downloaded to the cell phone 120 (or other computing device) from the internet.

The illustrated example system 100 includes a wrist-mounted device 110a. The wrist-mounted device 110a could take the form of a watch or fitness band and could include accelerometers, gyroscopes, or other sensors to detect the motion of the wrist, forearm, hand, or other body segment (s). The wrist-mounted device 110a could also include photoplethysmographic sensors, ECG electrodes, galvanic skin response electrodes, or other sensors for generating signals related to the operation of the autonomic nervous system, heart, cardiovascular system, or other portions of the wearer's 105 body. For example, the wrist-mounted device 110a could include a photoplethysmographic sensor configured to detect an amount of blood in subsurface vasculature of the wrist as well as to detect an oxygenation state of the blood. The wrist-mounted device 110a could further include ECG electrodes.

The illustrated example system 100 includes an ankle-mounted device 110b and a torso-mounted device 110c. These devices could include accelerometers, gyroscopes, inertial measurement units, or other sensors to measure the acceleration, orientation, or other information about the motion or location of the ankle and torso, respectively, of the wearer 105. The torso-mounted device 110c could additionally include ECG electrodes to detect the electrical activity of the wearer's 105 heart, strain gauges or other strain-sensitive elements to detect the wearer's 105 breaths, or some other sensors.

The illustrated example system 100 includes a patch device 110d mounted, by an adhesive, to skin of the wearer's 105 upper arm. The patch device 110d could include a thermometer to detect the temperature of the wearer's 105 skin. The patch device 110d could additionally or alternatively include a penetrating sensor configured to detect an amount of glucose or other analytes in the wearer's 105 body (e.g., in the wearer's 105 blood) when the penetrating sensor is inserted into the surface of the wearer's 105 skin.

The system 100 could determine that the wearer is performing or otherwise engaged in a particular activity during one or more periods of time. Such a determination could be based on user inputs (e.g., a person indicating that they are about to perform a particular diagnostic task or exercise), on one or more signals generated by one or more sensors of the system 100, or on some other source of information (e.g., on the identity of wireless networks that are visible to the cell phone 120). Such activities could include sleeping, exercising, running, walking, locomoting, resting, cooking, typing, bathing, driving a vehicle, or some other activity.

Based on the determination that the wearer is, during a particular period of time, performing or otherwise engaged in a particular activity, the system 100 could detect, based on one or more signals generated by one or more sensors of the system 100, discrete events that are related to the particular activity and that occur during the particular period of time. The discrete events could be related to a disease or other health state of interest. The events could be related to actions performed or tested in a clinical environment in order to assess the health state of interest. Additionally or alternatively, it could be determined, based on sensor signals recorded from a population of wearers, that the events are related to the health state of interest. For example, to assess the presence, progression, or other properties of a movement disorder (e.g., Parkinson's disease, dystonia, essential tremor, chorea, dyskinesia, or some other movement disorder), the events could include discrete motions or actions, e.g., footsteps, turns of the wearer's body, reaches or other arm motions, or other motions or actions engaged in by the wearer 105.

Characteristics of such events could be determined and used to determine the health state of interest (e.g., to determine the presence, type, degree, severity, progression, or other properties of a movement disorder or other disease state). For example, a duration of a stance or swing phase of number of detected footsteps during locomotion, a maximum acceleration of the ankle during an number of heel strikes of the foot during locomotion, a duration of a number of REM periods during sleep, a mean velocity of a number of discrete turns of a wearer's torso during locomotion, or some other characteristics of such events and/or of other events could be determined for each of a number of detected events. Samples of such determined characteristics could be generated and used, individually or in combination, to determine a disease or other health state of a wearer. Additionally or alternatively, information about the wearer's 105 performance of one or more prompted diagnostic motor tasks could be used to determine such a disease or other health state of the wearer.

Figure 1B:
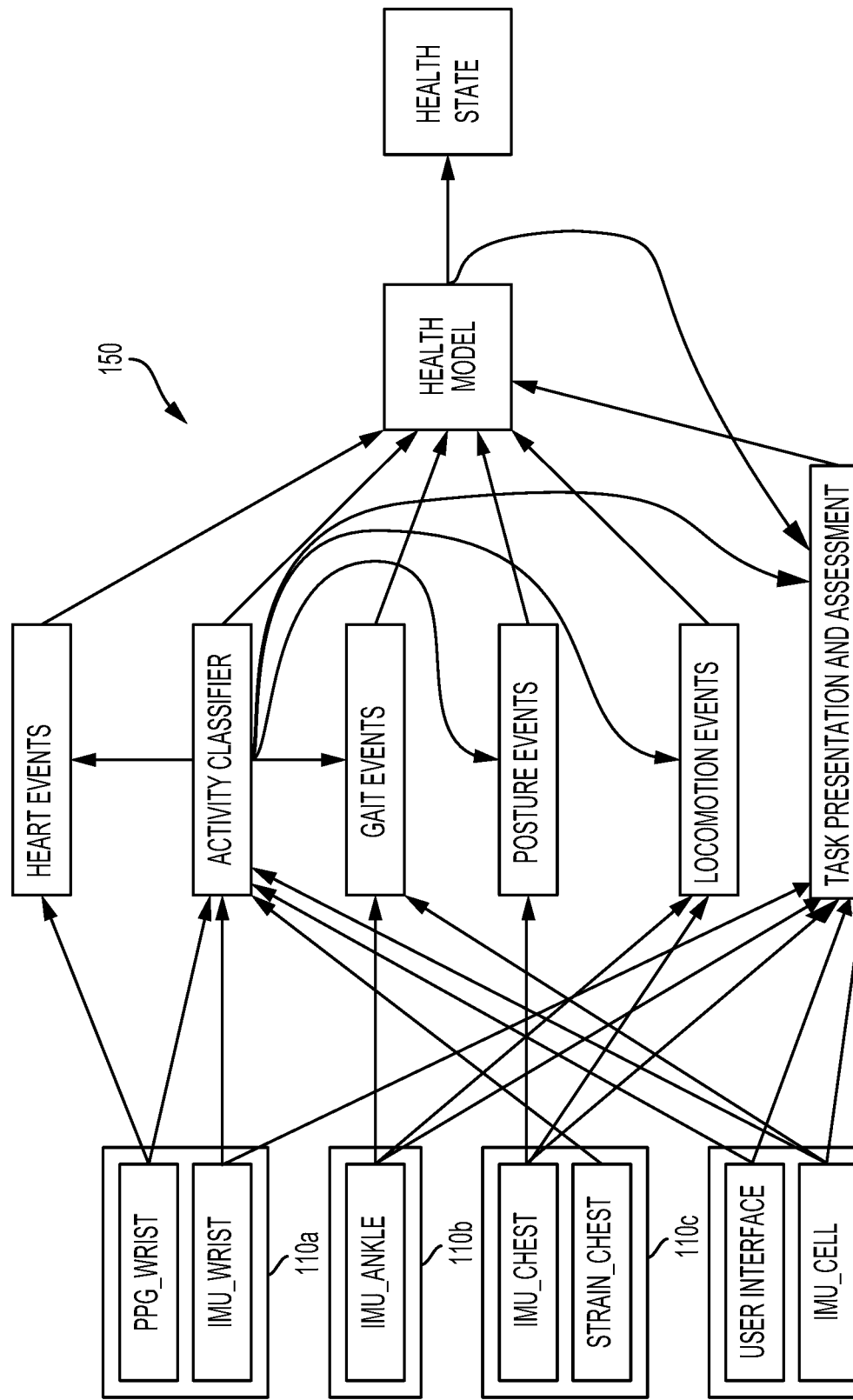
FIG. 1B illustrates a functional block diagram of elements of the example system of FIG. 1A and a method of processing signals generated by sensors of the example system.

FIG. 1B is a diagram that illustrates an example process 150 to determine, based on signals generated by sensors of the system, activities of the wearer 105, characteristics of events related to such activities, and a health state of the wearer 105 that is related to such events. Such a process 150 could be performed by a microprocessor or other computing device of the system 100 (e.g., of the cell phone 120). Sensors used in the illustrated process 150 include a photoplethysmographic sensor (PPG_WRIST) and inertial measurement unit (IMU_WRIST) in the wrist-mounted device 110a, an inertial measurement unit (IMU_ANKLE) in the ankle-mounted device 110b, a strain sensor (STRAIN_CHEST) and inertial measurement unit (IMU_CHEST) in the torso-mounted device 110c, and an inertial measurement unit (IMU_CELL) in the cell phone 120. A user interface (USER INTERFACE) of the cell phone 120 also provides information for the process 150.

An activity classifier (ACTIVITY CLASSIFIER) determines, based on a number of inputs, a particular activity of the wearer 105 during one or more periods of time. The activity classifier could be implemented as electronics (e.g., as a microcontroller executing instructions stored in a memory) disposed in one or more of the devices (e.g., 110a, 110b, 110c, 120) of the system 100. Additionally or alternatively, the activity classifier could be implemented on a server, on a personal computer, as instructions executed in a cloud computing service, or on some other system in communication with the system 100. As shown in FIG. 1B, the activity classifier receives signals related to accelerations and/or rotations of the cell phone 120, the torso-mounted device 110c, and the wrist-mounted device 110a, signals related to the heart and cardiovascular system from the wrist-mounted device 110a, and information related to user inputs to the cell phone 120. However, an activity classifier could receive additional or alternative signals or other information in order to determine an activity being performed or otherwise engaged in by a wearer.

Determining an activity could include performing filtering, preprocessing, or other processes to the signals or inputs received by the activity classifier. For example, a photoplethysmographic signal could be processed to determine a pulse rate, a pulse timing, a pulse rate variability, or some other information related to an activity of the wearer. Determining an activity could include applying the signals or inputs, or signals or information determined therefrom, to a threshold, a neural network, a pattern matching algorithm, a linear or nonlinear regression, a principal components analysis, or some other function, algorithm, or process. For example, the activity classifier could determine that a wearer is resting if a determined pulse rate is below a first threshold value or that the wearer is exercising if the pulse rate is above a second threshold value.

A task presentation and assessment module (TASK PRESENTATION AND ASSESSMENT) determines whether to prompt a wearer to perform one or more diagnostic motor tasks and, in response to determining that such a motor task should occur, prompts the wearer to perform the task and detects one or more signals related to the wearer's performance of the motor task. The task presentation and assessment module could be implemented as electronics (e.g., as a microcontroller executing instructions stored in a memory) disposed in one or more of the devices (e.g., 110a, 110b, 110c, 120) of the system 100. For example, a microprocessor of the cell phone 120 could operate to implement the task presentation and assessment module by executing instructions or other information downloaded from the internet. Additionally or alternatively, the activity classifier could be implemented on a server, on a personal computer, as instructions executed in a cloud computing service, or on some other system in communication with the system 100.

Determining whether to prompt a wearer to perform a specified motor task could include determining that motor activity of the wearer matches a stored pattern of motor activity in some respect (e.g., as regards a property of the motor activity, a distribution of a property of discrete events within the motor activity), differs from a stored pattern of motor activity, has changed relative to past activity, or making some other determination based on one or more sensor inputs of the system 100. Determining whether to prompt a wearer to perform a specified motor task could include comparing the wearer's motor activity during a particular period or duration of time (e.g., the wearer's motor activity across an hour) to a baseline activity profile or other information representative of the wearer's past motor activity.

Prompting the wearer can include operating the user interface of the cell phone 120 or operating some other component of the system 100 (e.g., a light, a display, a speaker, a buzzer, a vibrator, an electrohaptic user interface) to prompt the wearer to perform a motor task. Prompting a wearer could additionally include providing information about the performance of the motor task, e.g., the identity of the motor task, a particular location or duration of the motor task, the location of a target (e.g., an icon on a touch screen) of the motor task, a countdown or other information about the timing of the motor task (e.g., a tone or other indication of when the wearer should commence the motor task, or when the wearer should perform a particular element of the motor task), or some other information about the motor task. In some examples, the motor task could include interacting with elements of the system 100 (e.g., speaking into a microphone, interacting with the user interface of the cell phone 120, pressing a button or icon of a touch screen) and the prompt could indicate information about such an interaction. In such examples, the controller could additionally operate to provide indications related to the wearer's performance of the motor task, e.g., feedback related to the magnitude of a prompted force, the volume of prompted speech, or indications related to some other feedback.

The process 150 additionally includes detecting one or more signals from sensors of the system 100 related to the wearer's performance of a prompted motor task (TASK PRESENTATION AND ASSESSMENT). This may also include determining one or more properties of the performed motor task. For example, the process 150 could include determining a velocity of locomotion, a regularity in time or space of footsteps taken during locomotion, a magnitude or frequency of a tremor, a period of time taken to perform the prompted task, a latency between a prompt to perform a motor task and performance of such motor task, a period of time taken to stand and/or to sit, or some other information about the prompted motor task.

In some examples, one or more sensors of the system 100 could be operated to generate a signal in response to detecting a particular activity, e.g., to reduce a power or bandwidth requirement of the one or more sensors when the wearer is not performing or otherwise engaged in the particular activity. This could include activating, powering, communicating with, receiving signals from, or otherwise operating a sensor in response to the determined particular activity. Additionally or alternatively, this could include increasing or otherwise changing a sampling rate, resolution, signal-to-noise ratio, amplification, or other property of the operation of a sensor in response to detecting a particular activity.

Based on the determination that a wearer is performing or otherwise engaged in a particular activity (ACTIVITY CLASSIFIER), certain events related to the particular activity can be detected from the sensors signals. Additionally or alternatively, the determination that a wearer is engaged in a particular activity could be used to determine whether to prompt the wearer to perform a diagnostic motor task. The presence, timing, or other information about these events could be detected by performing a variety of operations on the sensor signals, e.g., pattern matching, convolution, filtering, domain transformation, thresholding, or some other processes to detect the presence of an event from one or more sensor signals.

For example, to detect a heartbeat, an instance of arrhythmia, or other heart-related events from a photoplethysmographic signal during a particular activity (e.g., when a wearer is engaged in strenuous exercise), a threshold could be applied to the signal in order to detect when the signal exceeds a threshold having a value related to the presence of a heartbeat in the photoplethysmographic signal. A timing, period, duration, timing variability, frequency, rate, or some other characteristic of each such detected heart event could then be determined and transmitted, logged, or used in some other manner.

In another example, to detect a wearer turning his or her body, losing balance, or other posture events from an acceleration, rotation, or other inertial signal from the torso-mounted device 110c during a particular activity (e.g., during locomotion), pattern matching could be applied to detect such events (e.g., to detect that a portion of an acceleration, rotation, or other signal corresponds to a pattern associated with such events). A maximum velocity, a mean velocity, a duration, a frequency, or some other characteristic of each such detected posture event could then be determined and transmitted, logged, or used in some other manner.

In yet another example, to detect a wearer taking a step, jumping, turning, stepping up, stopping, losing balance, or other locomotion events from an acceleration, rotation, or other inertial signal from the ankle-mounted device 110a and/or the torso-mounted device 110c during a particular activity (e.g., during locomotion), pattern matching could be applied to detect such events (e.g., to detect that a portion of an acceleration, rotation, or other signal corresponds to a pattern associated with such events). A step duration, a stance phase duration, a swing phase duration, a step length, a mean or maximum foot velocity, a step height, a frequency, a step duration variability, a mean or maximum ankle acceleration at lift-off, a mean or maximum ankle acceleration at heel strike, or some other characteristic of each such detected locomotion event could then be determined and transmitted, logged, or used in some other manner.

The process 150 also includes determining, based on one or more samples of such determined event characteristics and/or information about the wearer's performance of one or more prompted motor tasks, a health state of a wearer using a health model. The health model could be implemented as electronics (e.g., as a microcontroller executing instructions stored in a memory) disposed in one or more of the devices (e.g., 110a, 110b, 110c, 120) of the system 100. For example, a microprocessor of the cell phone 120 could operate to implement the health model and/or to perform processes thereof by executing instructions or other information downloaded from the internet. Additionally or alternatively, the health model could be implemented on a server, on a personal computer, as instructions executed in a cloud computing service, or on some other system in communication with the system 100.

Using such a health model could include determining a mean, standard deviation, distribution shape, or other properties of one or more of the samples of characteristics and/or of the information detected during the wearer's performance of the prompted motor task(s). The health model could apply such determined properties, or the sensor signals themselves, to a linear regression model, a nonlinear regression model, a neural network, a principal components model, or some other model or algorithm to generate a disease severity score or other health state information. The health model could receive multiple different samples of the same characteristic from the same wearer that were generated during different periods of time, that correspond to different activities, or that differ with respect to some other consideration. For example, the health model could compare different samples of the same characteristic that were generated during different, non-overlapping periods of time in order to determine an amount of progression of a disease.

Additionally or alternatively, the process 150 could include determining a clinical standard score or some other rating of a wearer's disease state and/or performance of one or more motor tasks. For example, the process 150 could include determining a UPDRS and/or MSFC score for the wearer. Such a score or rating could be determined based on known relationship between measured and/or determined properties of the wearer's motor activities and the corresponding score or rating (e.g., based on relationship determined by measuring both the score or rating for a population of wearers and determined properties of the wearers' motor activities). Alternatively, such a score or rating could be determined directly from information detected during the wearer's performance of one or more motor tasks that are traditionally used, in clinical settings, to determine such a score or rating. For example, the process 150 could include prompting the wearer to perform the UPDRS and/or MSFC assessment tasks and detecting one or more signals related to the wearer's performance of the prompted tasks, such that a UPDRS and/or MSFC score may be determined, from the detected one or more signals, based on the wearer's performance of the prompted UPDRS and/or MSFC assessment tasks.

The structure, parameters, or other properties of the health model could be determined based on past information from one or more wearers, e.g., the health model could provide an output that is predictive of whether a wearer's health state is significantly different from the wearer's health state in the past and this output could be used to determine that the wearer should seek medical attention, take a drug, or pursue some other action. The health model could be used to generate a baseline activity profile that represents one or more properties of a wearer's usual motor activity, and the process 150 could include comparing the wearer's ongoing motor activity to the determined baseline activity profile in order to determine when to prompt the wearer to perform one or more diagnostic motor tasks. The health model could additionally or alternatively be based on epidemiological or other medical information about a population of persons, e.g., a population of persons that are related to a wearer according to demographics. The health model could be updated based on changes in such information, e.g., based on additional data received from a population of wearers of the devices and systems described herein.

The process 150 and/or particular elements thereof (e.g., one or more of the elements illustrated in FIG. 1B) could be performed by a controller of the system 100 (e.g., a controller disposed in the cell phone 120). Additionally or alternatively, some elements of the process 150 could be performed by a remote system, e.g., by a server, cloud computing service, or other remote system that is in communication with the system 100. For example, the system 100 could transmit, to such an external system, indications of sensor signals (e.g., signals detected during performance of a prompted motor task), determined activities, determined events and/or characteristics thereof and the external system could then, based on such transmitted information, determine a health state of the wearer 105, a baseline activity profile of the wearer 105, or some other information about the wearer 105. Such determined information could then be transmitted to the system 100 (e.g., to the cell phone 120). The system 100 could additionally or alternatively receive programming, health models or parameters thereof, baseline activity profiles or parameters thereof, activity classifiers or parameters thereof, event detection models or algorithms, motor task prompts and/or assessment algorithms, or some other information from such external systems and such received information could be used, by a controller of the system 100, to perform one or more elements of the process 150. Such information could be determined, by the external system, based on health information, sensor signals, or other information from the wearer 105, based on health information, sensor signals, or other information from a population of wearers, or based on some other information.

Note that the configurations and operations of sensors, controllers, or other elements of a system as described herein are meant as non-limiting examples.

III. EXAMPLE SIGNALS

A variety of signals related to motor activity of a person may be detected, using the methods and systems described herein, and used to determine whether to prompt the person to perform a diagnostic motor task. Such signals may be related to motion of parts of the person's body (e.g., acceleration, rotation, location of parts of the person's body), physiological properties of the person's body (e.g., heart rate, breathing rate, oxygen saturation), sounds generated by the person (e.g., during speech), forces exerted by the person (e.g., to push an object, to type on a keyboard, to interact with a touch screen), or some other properties related to motor activities of the person. Such signals may also be used to determine a health state, a property of a disease state or process (e.g., of a movement disorder), or to determine some other information about the person.

In order to use such signals to determine when and/or whether to prompt the person to perform a motor task (e.g., a diagnostic motor task related to a disease state or process, or to some other health state of the person), the signals could be detected during a first period of time and used to obtain a baseline activity profile that is representative of the motor activity of the person during the first period of time. During a second, subsequent, period of time, the signals could be detected again and the motor activity of the person during the second period of time could be compared to the baseline activity profile to determine whether to prompt the person to perform a motor task. For example, the person could be prompted to perform a diagnostic motor task due to one or more properties of the motor activity during the second period of time differing from corresponding properties of the motor activity represented by the baseline activity profile. One or more signals related to the person's performance of the motor task could then be detected and used to determine some information about the person, e.g. to determine a standard clinical rating or score, or to determine some other information related to the presence, progression, severity, or other properties of a disease state or process. The one or more signals related to the prompted motor task may be the same as the signals used to determine the baseline activity profile and to determine whether to provide the motor task prompt, or they may be different signals.

Figure 2:
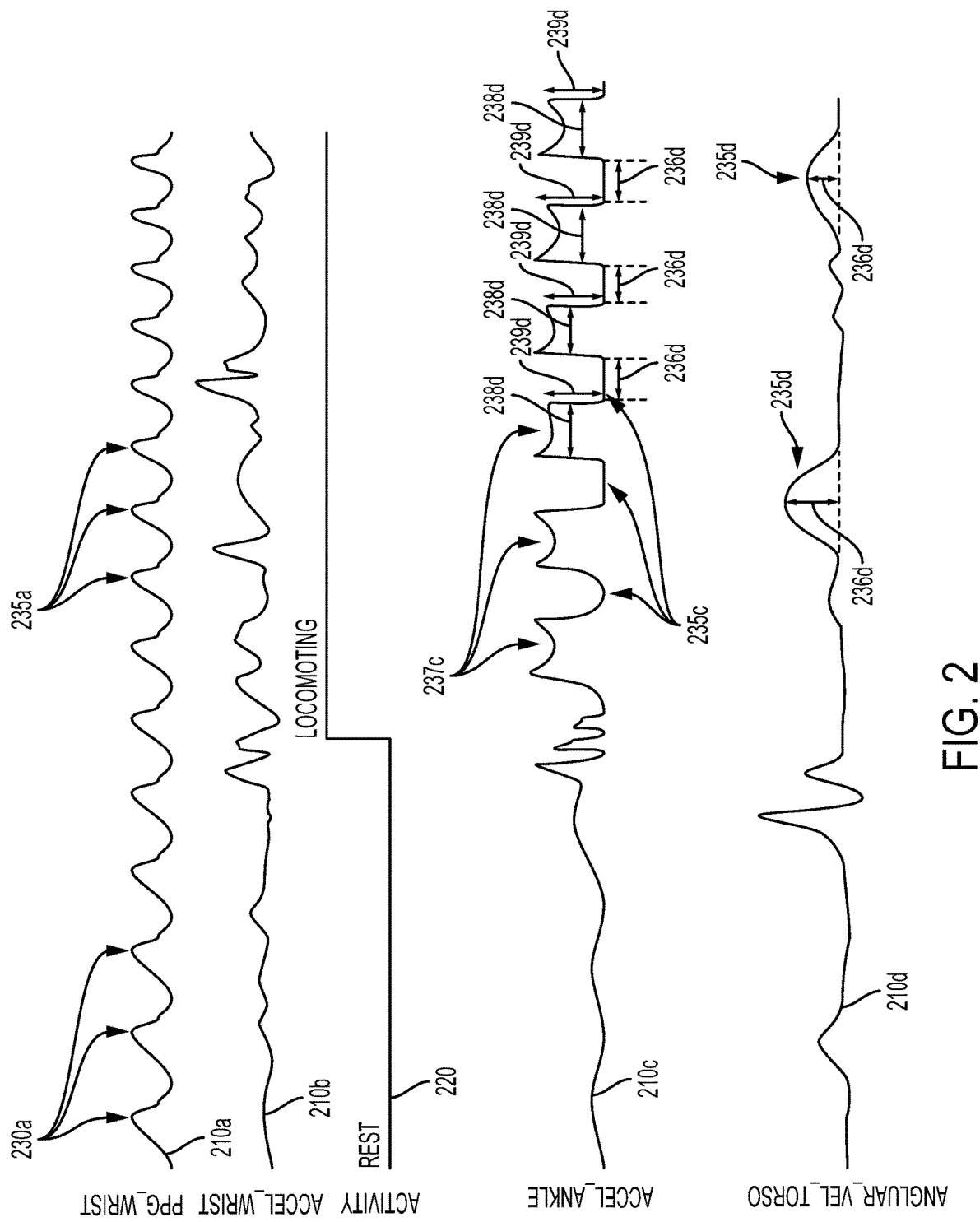
FIG. 2 illustrates example signals.

FIG. 2 illustrates a number of example signals that could be received (e.g., by a controller of a device or system of body-mountable or otherwise configured devices as described herein) and used to determine an activity of a person, to determine a health state of such a person, to determine whether to prompt such a person to perform a diagnostic motor task, to assess the performance of such a motor task, or to facilitate some other application. The example signals include a photoplethysmographic signal detected from subsurface vasculature of a wrist ($210a$) and a magnitude of the acceleration of the wrist ($210b$). The example signals also include a magnitude of the acceleration of an ankle ($210c$) and a magnitude of an angular velocity of a torso ($210d$), e.g., around the long axis of the torso. As shown in FIG. 2, a person from whom the signals are detected (e.g., using body-mountable devices mounted to a wrist, ankle, and torso of the person, using a cell phone or other device located in a pocket of or otherwise coupled to a garment worn by the person) is resting during a first period of time and then and transitions to locomoting (e.g., walking, running).

One or more of the signals could be used to determine a particular activity of the person (e.g., to determine that the person is resting or locomoting), to determine that the person should be prompted to perform a diagnostic motor task (e.g., to determine that the person has, in the last hour, day, or other specified period of time, engaged in locomotion significantly less than usual), or to facilitate some other application. For example, the photoplethysmographic signal $210a$ and magnitude of the acceleration of the wrist $210b$ could be used to determine the activity of the person. This could include detecting individual heartbeat events $230a$, $235a$ to determine a pulse rate and determining an overall power in the acceleration signal $210b$. The locomoting activity could be determined if the power in the acceleration signal $210b$ is greater than a threshold and/or the pulse rate is greater than a threshold. This is illustrated by the activity trace 220 illustrated in FIG. 2. Some other method could be used to determine a particular activity of the person based on one or more signals generated by one or more sensors.

Depending on the determined activity at a particular time, the person could be prompted to perform a motor task. Additionally or alternatively, one or more discrete events can be detected, based on the determined activity at a particular time, in one or more of the sensor signals $210a$, $210b$, $210c$, $210d$. For example, discrete turns of the person's torso $235d$ could be detected from the magnitude of a rotational velocity of a torso $210d$ during the locomotion activity. Individual heartbeat events could be detected during the rest activity $230a$ and/or during the locomoting activity $235a$. Individual footstep events, or discrete events within each footstep, could be detected during the locomotion activity. This could include detected stance phases $235c$ and swing phases $237c$. Other events could be detecting in the illustrated signals, or in additional signals, during periods of time when a person is resting, locomoting, exercising, sleeping, or performing or otherwise engaged in some other activities.

For each detected event during a particular determined activity, one or more characteristics could be determined. Such characteristics could be related to a disease or to some other health state, and a sample of such determined characteristics could be used to determine information about the health state of a person. Additionally or alternatively, a sample of such determined characteristics, detected during a particular time, could be compared to a baseline activity profile and used to determine whether to prompt a person to perform a diagnostic motor task. Such characteristics could be determined from properties of each individual detected event, from the relationship between each detected event and one or more other detected events, or based on some other property of the detected events. For example, the duration of each swing phase $238d$ and/or the duration of each stance phase $236d$ could be determined. In another example, the magnitude of the acceleration of the ankle at the end of the swing phase $239d$ (e.g., when the heel strikes the ground) could be determined. In yet another example, a maximum angular velocity of each discrete turn of the person's torso $236d$ could be determined, or the mean angular velocity of the person's torso during each such turn, or some other characteristic of turns of other events determined from the rotational velocity of the torso could be determined.

A sample of such determined characteristics of a particular event related to a particular activity (e.g., locomotion) could be determined and used to determine a health state or some other property of a person, to determine a baseline activity profile of a user, to determine whether to prompt a user to perform a diagnostic motor task (e.g., based on a previously determined or otherwise obtained baseline activity profile of the user), or to facilitate some other application. Further samples of determined characteristics of different events detected in signals from different sensors, of determined characteristics of different events detected in signals from the same sensor, of determined characteristics of similar events detected in signals from the same sensor during a different event, or of some other determined characteristics could additionally be used to determine such a health state, to provide such a prompt, or to facilitate some other application. This could include determining a mean or other statistical property of the samples and applying such a determined property to a regression model or to some other model or algorithm.

Figure 3:
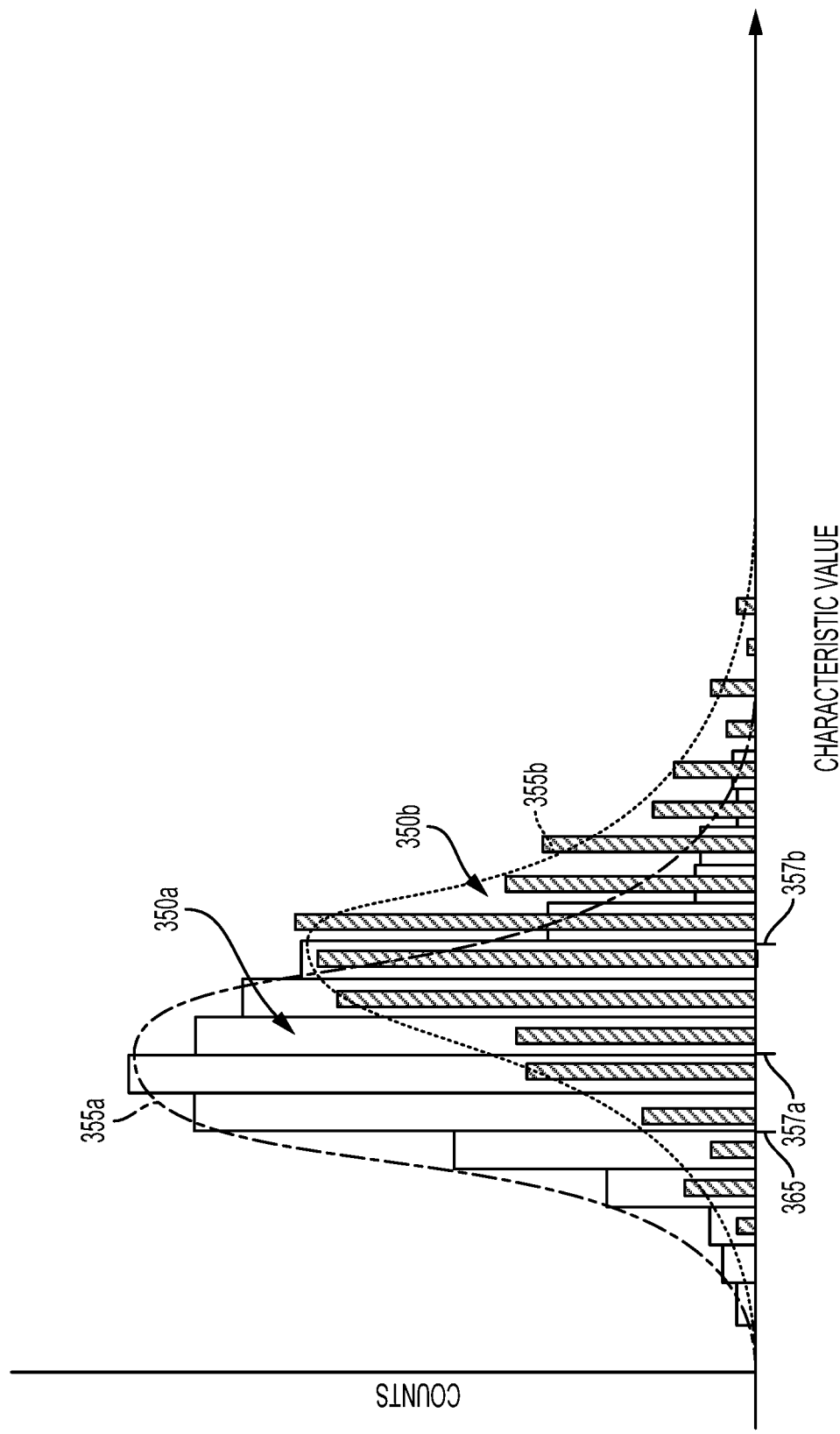
FIG. 3 illustrates example clinical data.

FIG. 3 illustrates the values of first $350a$ and second $350b$ samples of characteristics determined as described herein. The samples are illustrated as histograms, indicating the number of events detected during a particular period of time and/or when a particular activity was detected having a determined characteristic value within each of a number of discrete ranges. The two different samples $350a$, $350b$, could be samples of different characteristics of the same event, samples of characteristics of different events (e.g., of events detected in different sensor signals), samples of characteristics of the same event detected in the same sensor signal but associated with different activities, samples of the same characteristic of the same event and associated with the same activity but detected during different periods of time, or samples that differ with respect to some other factor(s). As shown, a mean $357a$, $357b$, fitted normal (or other) distribution $355a$, $355b$, standard deviation, or some other properties of the samples $350a$, $350b$ could be determined, e.g., to determine whether to prompt a person to perform a motor task, to determine the presence of a disease, the type of a disease, a severity of a disease, a degree of progression of a disease, to determine some other health state of a person, or to facilitate some other application.

In order to determine whether to prompt a person to perform a motor task, one or more properties of a signal related to motor activity of a person could be compared to a baseline activity profile determined previously for the person. Such a baseline activity profile could represent a mean, a pattern, a distribution, or some other information representative of the motor activity of the person during motor activity. For example, a baseline activity profile could include a mean, a standard deviation, a kurtosis, a range, or some other information about a sample of determined characteristics of events detected when the person is engaged in motor activity during a first period of time. Such characteristics could be determined for events detected during motor activity of the person during a second period of time, based on a comparison between the baseline activity profile and the determined characteristics for the second period of time, the person could be prompted to perform a motor task. Such a comparison could include determining that the determined characteristics for the second period of time differ from the baseline activity profile by more than a threshold amount, e.g., that a mean of the determined characteristics for the second period of time differs from a mean characteristic represented by the baseline activity profile.

For example, the first sample 350a could represent characteristics determined from motor activity events of a person (e.g., step durations determined from an ankle acceleration signal) that occurred during a first period of time. A baseline activity profile that includes the first mean 357a could be determined for the person based on the first sample 350a. The baseline activity profile could then be used to determine, based on future motor activity of the person, whether to prompt the person to perform a diagnostic motor task. For example, the second sample 350b could represent characteristics determined from motor activity events of the person that occurred during a second period of time. The second mean 357b could be determined for the person based on the second sample 350b and compared to the baseline activity profile. If a difference between the second mean 357b and the baseline activity profile (e.g., the first mean 357a of the baseline activity profile) is greater than a threshold amount, the person could be prompted to perform a diagnostic motor task.

IV. EXAMPLE TASKS AND TASK PROMPTS

In response to detecting a change in the motor activity of a person or determining that the motor activity of the person satisfies some other condition, the person could be prompted to perform a motor task. The person could be prompted to perform the motor task when such performance would be especially beneficial, e.g., during the occurrence of a particular symptom (e.g., a rare disease-related event), when a particular symptom or an overall disease severity changes (e.g., increases or decreases), when a symptom that is potentially related to the disease state or process changes, or at some other time when information detected about the disease state or process may be especially diagnostically relevant. By prompting the person to perform the motor task in response to determining some change or other property of the detected ongoing motor activity of the person, the person's compliance with performing such a diagnostic motor task, a quality of performance of the motor task by the person, or some other property of the motor task and/or of the person's performance thereof could be improved.

The person could be prompted to perform one or more of a variety of different motor tasks. In some examples, the motor tasks could include executing specified motor tasks. For example, the motor task could include touching the tips of the person's opposite hands together, the person touching their nose, the person holding their arm(s) out straight in front of themselves, the person speaking a certain phrase, the person touching a particular icon or button on a keyboard or other user interface, the person typing a particular phrase using a keyboard, the person standing up from a sitting stance or sitting down from a standing stance, or some other specified motor task. Additionally or alternatively, the motor tasks could include the person executing spontaneous motor activity, e.g., speaking unprompted, typing a user-selected phrase, performing a user-selected activity of daily living, or some other activity at least partially specified by the person. Specified motor tasks could include elements of a clinical assessment, e.g., the motor task could include one or more tasks from the UPDRS, the MSFC, or some other clinical assessment.

Prompting a person to perform a motor task could include providing a prompt that the person should engage in the motor task or could include additional information. For example, providing a prompt to a person could include indicating the identity of the motor task to be performed (e.g., identifying which of an enumerated set of motor tasks the person should perform), indicating a timing of performance of the motor task (e.g., to allow a latency or other information about the timing of performance of the task, relative to the prompt, to be detected), indicating a location or target of the motor task (e.g., indicating a particular key or icon to be pressed or otherwise interacted with on a keyboard or other user interface), indicating a particular phrase to be spoken or typed, indicating that the person should exert a maximal force or otherwise indicating a degree of exertion for performance of the motor task, or indicating some other information about the motor task to be performed by a person.

Information could be provided to a person during performance of a prompted motor task. For example, the person could be provided, while performing a motor task, with feedback regarding the magnitude of a force exerted by the person, a height or length of a step taken by the person, an amplitude of speech or other sounds generated by the person, a location of a part of the person's body, or some other information about the person's body and/or the person's performance of a prompted motor task. Such information, provided during performance of the prompted motor task, could form part of the motor task itself, e.g., the motor task could include controlling a magnitude of force exerted, an amplitude of speech generated, a direction and/or destination to which to drag an icon on a touchscreen, or performing some other task based on such provided information.

In some examples, the prompted motor task could include a motor task. For example, the motor task could include a person getting up from a sitting stance and beginning to walk (e.g., a "timed-up-and-go" task); a person walking a specified distance from a starting point, turning around, and walking back to the starting point; a person sitting down or engaging in some other transfer activity (e.g., to or from a bed, wheelchair, chair, or automobile); a person locomoting while using a walker or other assistive device that may, itself, be instrumented; a person standing still or performing some other task while on a balance board that may be instrumented (e.g., with one or more load cells or other force sensors); or a person engaging in some other locomotive activity. An acceleration, a rotation, a force (e.g., a force between a person's foot and the floor), a location, or some other signal related to one or more body parts of the person could be detected and used to assess the performance of such a motor task, e.g., to determine a severity or degree of progression of a movement disorder or other disease state or process. Such a detected signal could be used to determine an amount of tremor, an amount of ataxia, a gait period or variability, a step height or length, a speed of walking, an amount of side-to-side motion during walking, a latency or other time characteristic of performance of the motor task following a prompt, or some other property of the person's performance of the prompted motor task.

In some examples, the motor task could include engaging in upper-limb motor activities. For example, the motor task could include the person tapping their nose; the person interacting with a keyboard, touchscreen, or other user interface; the person tapping their fingers; the person holding their arm(s) out and holding their arm(s) motionless; the person opening a door, using an eating utensil, the person writing long hand, or the person performing some other activity of daily living; or a person engaging in some other motor activity involving their upper limb(s). An acceleration, rotation, or location of one or more body parts of the person, a force (e.g., a force between a person's hand and an eating utensil, or between an eating utensil and a plate, or a force between a person's finger and a touch screen) exerted by the person, an output of a button (e.g., a button of a keyboard), a location at which a person is touching a touchscreen or other user interface, or some other signal related to the person's performance of the motor task could be detected and used to assess the performance of such a motor task, e.g., to determine a severity or degree of progression of a movement disorder or other disease state or process. Such a detected property could be used to determine an amount of tremor, an amount of ataxia, typing speed, a manual dexterity, an amount of side-to-side motion while performing an activity of daily living, a latency or other time characteristic of performance of the motor task following a prompt, or some other property of the person's performance of the prompted motor task.

In some examples, the motor task could include speaking or otherwise generating sounds (e.g., humming, singing). For example, the motor task could include the person speaking extemporaneously; the person reciting an indicated text (e.g., reciting words indicated on a display of a cell phone or other device); the person humming or producing a tone; the person yelling; the person humming, producing a tone, and/or speaking at a specific volume level or at a specified tone; or a person producing some other sounds. An amplitude, a frequency, a spectrum, a pressure waveform, or some other signal related to the person's performance of the motor task could be detected (e.g., using a microphone) and used to assess the performance of such a motor task, e.g., to determine a severity or degree of progression of a movement disorder or other disease state or process. Such a detected property could be used to determine an amount of vocal tremor, degree of tonal control, a volume of speech, a speed of speech, a degree of elocution and/or slurring of speech, a latency or other time characteristic of performance of the motor task following a prompt, or some other property of the person's performance of the prompted motor task.

The person could be prompted to perform a diagnostic motor task when such performance would be especially beneficial, e.g., during the occurrence of a particular symptom (e.g., a rare disease-related event), when a particular symptom or an overall disease severity changes (e.g., increases or decreases), when a symptom that is potentially related to the disease state or process changes, or at some other time when information detected about the disease state or process may be especially diagnostically relevant. In order to determine that a person should be prompted to perform a diagnostic motor task, one or more signals related to the person's motor activity (e.g., to motion of one or more body segments of the person, to a force exerted by the person, to speech or other sounds generated by the person, to a person's interaction with a user interface or other device, to a pulse rate or other physiological property related to motor activity) could be detected and used to determine whether to prompt the person to perform a motor task.

Determining whether to prompt a person to perform a motor task could include comparing the person's motor activity during a particular period of time to prior motor activity of the person. For example, an amount of time spent locomoting or performing some other task during a specified period of time (e.g., during an hour) could be compared to the amount of time spent locomoting during prior periods of time (e.g., during one or more previous hours). Such a comparison could include determining a property of the person's motor activity during a particular period of time and comparing a corresponding property of the person's motor activity during a previous period of time, e.g., determining that the property of the person's motor activity during the particular period of time is less than the corresponding property of the person's motor activity during the previous period of time by more than a threshold amount. Comparing a person's motor activity during different periods of time could include performing pattern matching (e.g., to determine whether a gait pattern of the person during a first period of time differs from or corresponds to a gait pattern determined for a second period of time), comparison of a level or direction of a detected or determined property of the person's motor activity (e.g., comparing a determined average turn velocity during a first period of time to a determined average turn velocity during a second period of time), or performing some other determination.

In some examples, a baseline activity profile or other information representative of the person's usual motor activity could be determined, during a first period of time, based on detected signals related to the person's motor activity during the first period of time (e.g., days, weeks, or some other period of time). Such a baseline activity profile or other representative information could include an amount of time usually spent by the person engaged in locomotion during a day, an amount of tremor usually present in the person's motions, a usual amplitude of the person's voice while speaking on the phone, an average length or duration of the person's steps during locomotion, a distribution of the length or duration of the person's steps during locomotion, or some other information about the person's motor activities during a period of time. The person's motor activity during a second, subsequent period of time could then be compared to the baseline activity profile or other determined representative information (e.g., based on detected signals related to the person's motor activity during the first period of time) and that comparison could be used to determine whether to prompt the person to perform a motor task.

Figure 4:
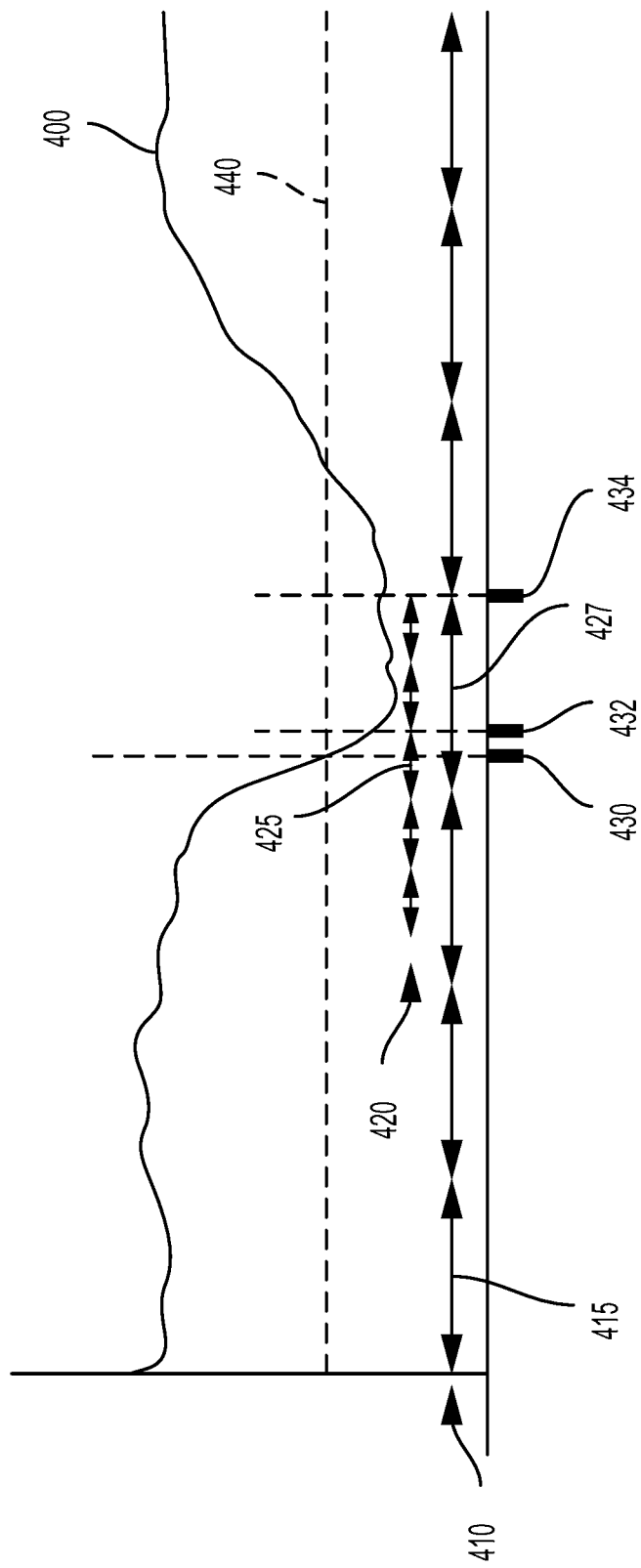
FIG. 4 illustrates an example signal.

FIG. 4 illustrates an example signal 400 related to a person's motor activity. The signal 400 could be an output from a sensor (e.g., an output of an accelerometer that is related to the amplitude of a tremor exhibited by the hand or arm of the person) or the signal 400 could be a property of the person's motor activity determined from one or more sensor signals (e.g., a continuously or near-continuously determined fraction of time the person spent engaged in locomotion during a previous period of time). FIG. 4 also shows a threshold level 440 of the signal 400, a number of long time periods 410 (e.g., hour- or day-long time periods), a number of short time periods 420 (e.g., minute- or hour-long time periods), and a number of points in time 430, 432, 434 when the person could be prompted to perform a diagnostic motor task.

A baseline activity profile could be determined based on the signal 400a detected during a first period of time, e.g., during one or more of the illustrated long 410 or short 420 periods of time. For example, a baseline activity profile could be determined based on the signal 400 detected during the indicated 415 long period of time. In some examples, the baseline activity profile could be updated when additional portions of the signal 400 are detected. For example, the baseline activity profile could be updated such that the baseline activity profile is determined based on a portion of the signal 400 detected during a specified duration of time prior to a present period of time (e.g., based on portions of the signal 400 detected during previous hour(s), day(s), or week(s)). The baseline activity profile 440 could include the threshold 440 and/or could include determined information about the person's motor activity (e.g., a determined mean step length or duration) that could be used to determine the threshold 440 (e.g., by scaling the determined mean step length or duration).

Once a baseline activity profile or other information representative of the person's motor activity has been obtained (e.g., by determining the baseline activity profile based on the signal 400 detected during one or more periods of time), the signal 400 may be detected during a subsequent period of time and used to determine whether to provide a prompt to the person that the person should perform a diagnostic motor task. This could include using the signal 400 detected during the further period of time to determine that the person's motor activity during the further period of time differs in some respect from the person's motor activity during the period of time used to determine the baseline activity profile. Determining such a difference could include performing pattern matching on the signal 400, comparing the signal 400 and/or a property of the signal 400 (e.g., comparing the signal 400 during the further period of time to the threshold 440), or performing some other process based on the baseline activity profile and a portion of the signal 400 detected during the further period of time. Responsive to determining, based on the signal 400 received during the further period of time, that the motor activity of the person during the further period of time differs from the motor activity of the person during the period of time used to determine the baseline activity profile.

For example, the further period of time could be a period of time immediately before the signal 400a decreases below the threshold 440, and the person could be prompted to perform a diagnostic motor task at the first point in time 430. In another example, the further period of time could be the time period 425 of the short time periods 420 during which some property of the signal 400 (e.g., a mean of the signal 400 across the short time period 425) and/or of the motor activity of the person decreases below the threshold 440. In such an example, the person could be prompted to perform a diagnostic motor task at some point in time after the time period 425, e.g., the second point in time 432. In yet another example, the further period of time could be the time period 427 of the long time periods 410 during which some property of the signal 400 (e.g., a mean of the signal 400 across the time period 427) and/or of the motor activity of the person decreases below the threshold 440. In such an example, the person could be prompted to perform a diagnostic motor task at some point in time after the long time period 427, e.g., the third point in time 434.

V. EXAMPLE WEARABLE DEVICES

Systems as described herein can include multiple body-mountable (or wearable) or otherwise configured devices and/or other elements (e.g., controllers, cell phones, control pendants, communications bridges). Body-mountable devices as described herein can be configured to be mounted to an external body surface of a wearer and to enable a variety of applications and functions including generating, using one or more sensors, one or more signals related to properties of a body segment to which the device is mounted. Devices as described herein could enable a variety of applications, including communicating with other devices and/or controllers, detecting signals related to motor activity of a person, comparing motor activity of a person during a period of time to motor activity of the person during a previous period of time, prompting the person to perform a diagnostic motor task in response to such a comparison, detecting one or more signals related to the person's performance of the prompted motor task, determining a particular activity being performed by or otherwise engaged in by a wearer, detecting one or more events based on sensor signal(s), determining a disease severity or other health state of a wearer, or other functions.

Figure 5A:
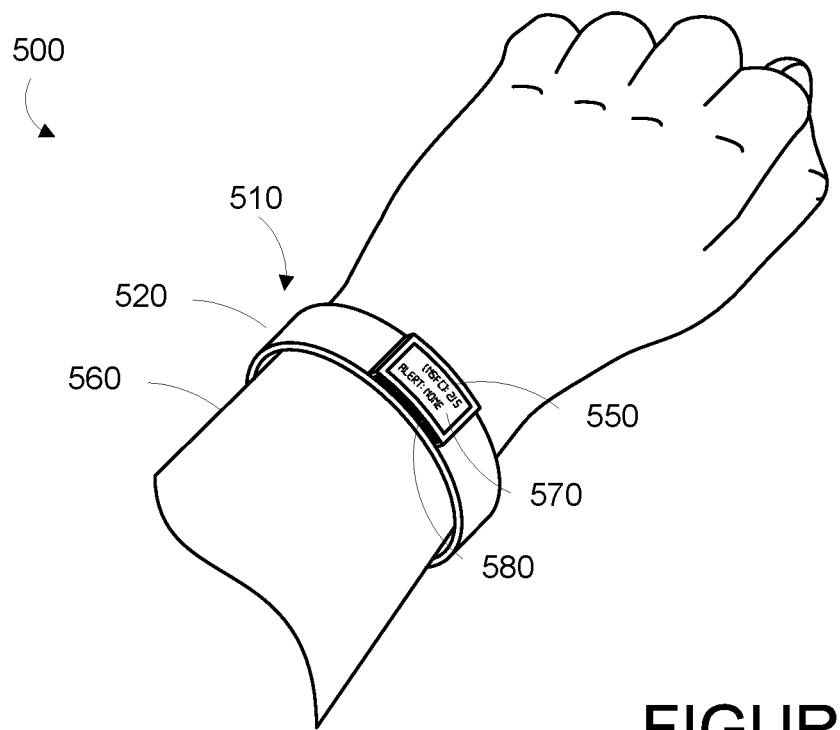
FIG. 5A is a perspective top view of an example wrist-mounted device, when mounted on a wearer's wrist.
Figure 5B:
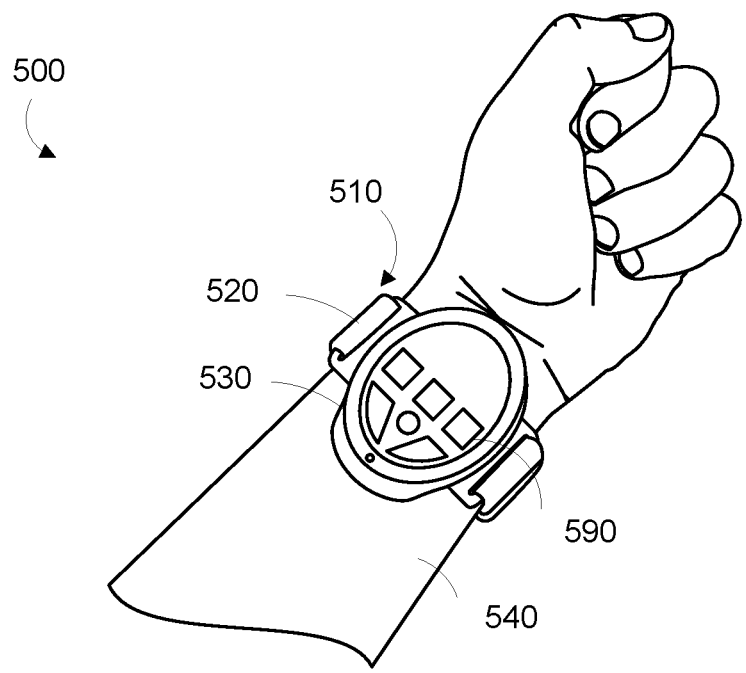
FIG. 5B is a perspective bottom view of the example wrist-mounted device shown in FIG. 5A, when mounted on a wearer's wrist.

In some examples, a system as described herein and/or one or more elements thereof are provided as a wrist-mounted device, as shown in FIGS. 5A and 5B. The wrist-mounted device may be mounted to the wrist of a living subject with a wristband or cuff, similar to a watch or bracelet. As shown in FIGS. 5A and 5B, the wrist mounted device 500 may include a mount 510 in the form of a wristband 520, a housing 530 containing a data collection system and positioned on the anterior side 540 of the wearer's wrist, and a user interface 550 positioned on the posterior side 560 of the wearer's wrist. The wearer of the device may receive, via the user interface 550, one or more recommendations or alerts generated either from a remote server or other remote computing device, prompts to perform a diagnostic motor task, indications related to performance of such a motor task, or alerts from the measurement platform. Such a configuration may be perceived as natural for the wearer of the device in that it is common for the posterior side 560 of the wrist to be observed, such as the act of checking a wrist-watch. Accordingly, the wearer may easily view a display 570 on the user interface. Further, the housing 530 may be located on the anterior side 540 of the wearer's wrist where the subsurface vasculature or other elements of the body of the wearer may be readily observable. However, other configurations are contemplated.

The display 570 may be configured to display a visual indication of an alert, recommendation, health state, or other information. Further, the user interface 550 may include one or more buttons 580 for accepting inputs from the wearer. For example, the buttons 580 may be configured to change the text or other information visible on the display 570. As shown in FIG. 5B, housing 530 may also include one or more buttons 590 for accepting inputs from the wearer. The buttons 590 may be configured to accept inputs for controlling aspects of the data collection system, such as indicating that the wearer is engaged in a particular activity, or inputs indicating the wearer's current health state (i.e., normal, migraine, shortness of breath, heart attack, fever, "flu-like" symptoms, food poisoning, etc.). Additionally or alternatively, the buttons 590 or other elements of a user interface of the device 500 could be used to detect signals related to a wearer's performance of a prompted motor task.

Figure 6:
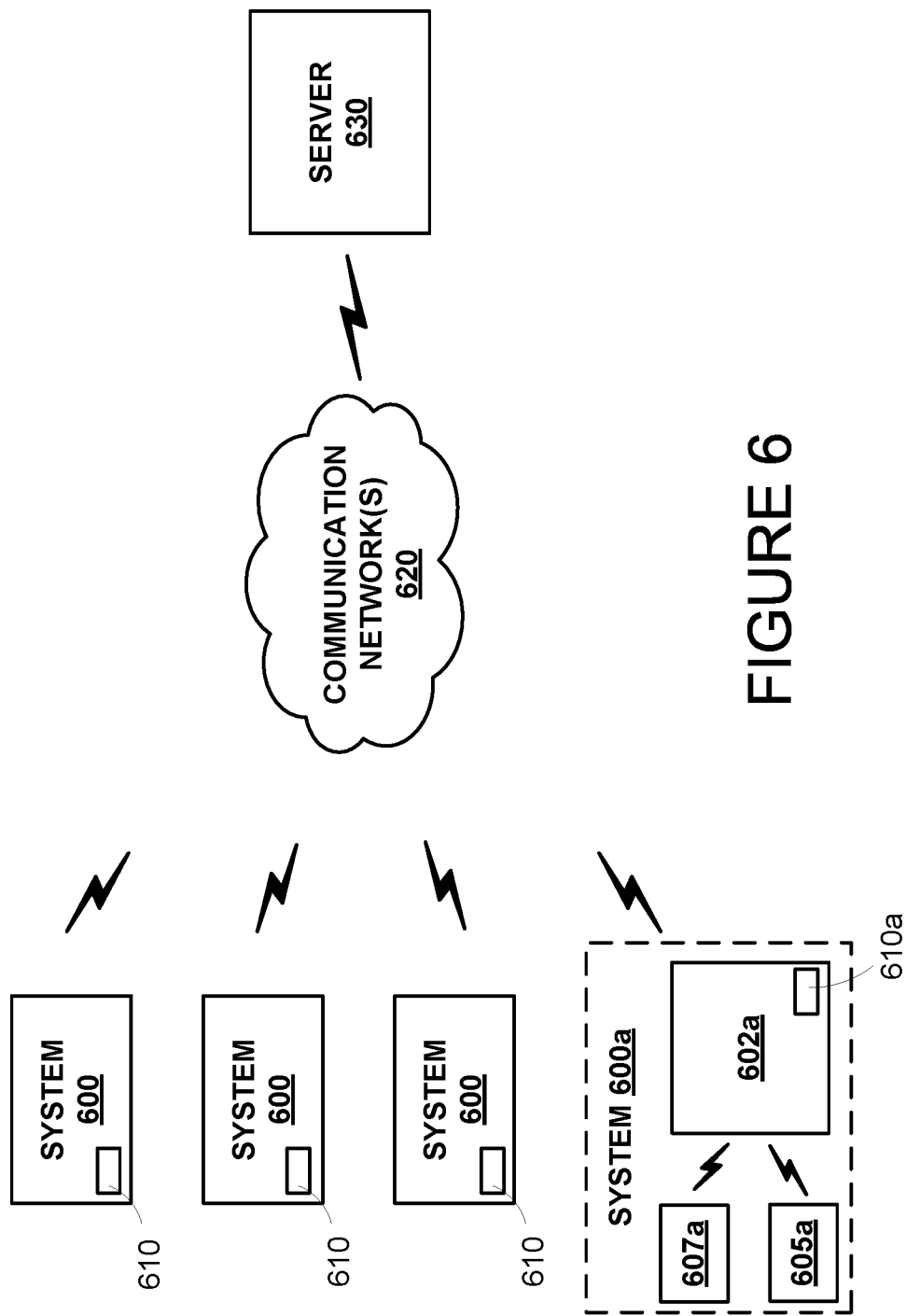
FIG. 6 is a block diagram of an example system that includes a plurality of devices in communication with a server.

FIG. 6 is a simplified schematic of a number of systems 600 each including one or more sensors configured to detect signals related to motor activity of respective persons and/or to detect signals related to such persons' performance of prompted motor tasks. In some examples, such sensors or other elements (e.g., a controller, a transceiver) of the systems 600 could be disposed in a cell phone or other device. Additionally or alternatively, such sensors or other elements of the systems 600 could be disposed in body-mountable devices worn by, mounted to the body of, or otherwise associated with respective persons.

The systems 600 may include a controller 610 configured to receive signals from one or more sensors of one or more devices (e.g., body-mountable devices) of each system 600. The controller 610 may additionally operate to transmit indications of the received signals, to determine a particular activity of a person based on one or more of the received signals, to determine that a person should be prompted to perform a diagnostic motor task and/or to provide such a prompt, to facilitate such a prompted motor task by providing indications related to the motor task, to detect one or more signals related to a person's performance of a prompted motor task, to determine a health state of a person from such signals, to transmit indications of any or all of the above information via a communication interface (e.g., a cellular radio link, a WiFi radio link) over one or more communication networks 620 to a remote server 630 and/or to received information (e.g., baseline activity profiles) from the remote server 630.

The controller 610 could be disposed in a body-mountable device and/or could be disposed in some other device (e.g., a cell phone). In one embodiment, the controller 610 includes a wireless transceiver for sending and receiving communications to and from the server 630. In further embodiments, the controller 610 may include any means for the transfer of data, including both wired and wireless communications. For example, the controller may include a universal serial bus (USB) interface or a secure digital (SD) card interface. Communication networks 620 may be any one of may be one of: a plain old telephone service (POTS) network, a cellular network, a fiber network and a data network. The server 630 may include any type of remote computing device or remote cloud computing network. Further, communication network 620 may include one or more intermediaries, including, for example wherein a system 600 transmits data to a mobile phone or other personal computing device, which in turn transmits the data to the server 630.

Each system 600 could include a single device or could include multiple devices in communication with each other. For example, example system 600a includes a controller 602a in wireless communication (e.g., using the Bluetooth communication standard) with two body-mountable devices 605a, 607a (e.g., a wrist-mounted device and an ankle-mounted device). The controller 602a includes a transceiver 610a as described above. The transceiver 610a could also be configured and/or operated to facilitate wireless communication with the body-mountable devices 605a, 607a. Alternatively, the controller 602a could include further components (e.g., further transceivers) to facilitate such communication. The controller 602a could be configured as a body-mountable device (e.g., a wrist-mounted device, a chest-mounted device) or could be configured in some other way. For example, the controller 602a could be a cell phone running software to provide the functions described herein.

In addition to receiving communications from a system 600, such as collected sensor signals or other collected physiological properties and data regarding health state as input by the person and/or one or more properties of a wearer detected using sensors disposed in body-mountable devices of the system 600, the server 630 may also be configured to provide some information to the system 600. This could include determining and transmitting to the system 600, based on signals received from the system 600, a health state of a person, a degree of severity or progression of a disease or disease state (e.g., Parkinson's disease, multiple sclerosis, ataxia, dystonia, or some other movement disorder), a health recommendation (e.g., a recommendation that the person take a drug), or some other information about the person. Additionally or alternatively, the server 630 could determine, based on signals received from the system 600, and transmit to the system 600 a baseline activity profile or other information indicative of a person's usual pattern of motor activity. The system 600 could then use such transmitted information to determine, based on further detected motor activity of the person, whether to prompt the person to perform a diagnostic motor task.

The server 630 may also be configured to gather and/or receive either from the system 600 or from some other source, information regarding a person's overall medical history, environmental factors and geographical data. For example, a user account may be established on the server for every person that contains the person's medical history. Moreover, in some examples, the server 630 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a person's health state from a hospital or physician. Such information may be used in the server's decision-making process, such as recognizing correlations and in generating clinical protocols.

Additionally, the server may be configured to gather and/or receive the date, time of day and geographical location of each person during each measurement period. Such information may be used to detect and monitor spatial and temporal spreading of diseases. As such, the system of body-mountable devices may be configured to determine and/or provide an indication of its own location. For example, a system of body-mountable devices may include a GPS system so that it can include GPS location information (e.g., GPS coordinates) in a communication to the server. As another example, a system of body-mountable devices may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a person. From this information, the server may be configured to derive an indication of the effectiveness of the drug or treatment. If a person is prescribed a drug intended to treat the symptoms of multiple sclerosis, but the server receives data from the system of body-mountable devices indicating that the person's symptoms have been increasing over a certain number of measurement periods, the server may be configured to derive an indication that the drug is not effective for its intended purpose for this person.

Further, some embodiments of the system may include privacy controls which may be automatically implemented or controlled by the person. For example, where a person's collected health state data are uploaded to a cloud computing network for trend analysis by a clinician, the data may be treated in one or more ways before it is stored or used, so that personally identifiable information is removed. For example, a person's identity may be treated so that no personally identifiable information can be determined for the person, or a person's geographic location may be generalized where location information is obtained (such as to a city, ZIP code, or state level), so that a particular location of a person cannot be determined.

Additionally or alternatively, users of a system of body-mountable devices may be provided with an opportunity to control whether or how the system collects information about the person (e.g., information about a person's medical history, social actions or activities, profession, a person's preferences, or a person's current location), or to control how such information may be used. Thus, the person may have control over how information is collected about him or her and used by a clinician or physician or other user of the data. For example, a person may elect that data, such as health state properties, collected from his or her device may only be used for generating an individual baseline and recommendations in response to collection and comparison of his or her own data and may not be used in generating a population baseline or for use in population correlation studies.

VI. EXAMPLE ELECTRONICS

Figure 7:
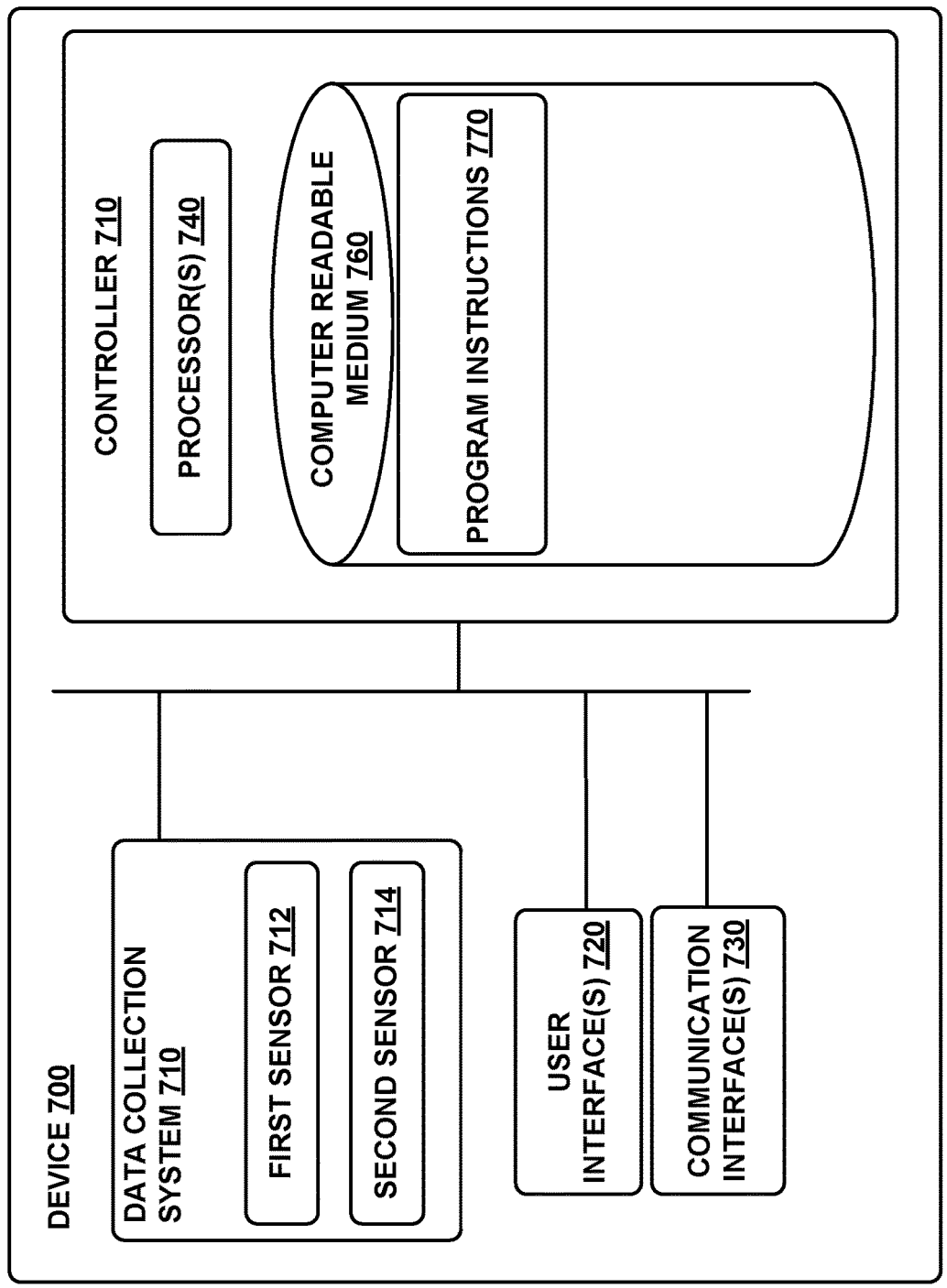
FIG. 7 is a functional block diagram of an example device.

FIG. 7 is a simplified block diagram illustrating the components of a device 700, according to an example embodiment. Device 700 may take the form of or be similar to one of the body-mountable devices 110a, 110b, 110c, 110d, 500 shown in FIGS. 1A, 1, and 5A-B. However, device 700 may also take other forms, such as an ankle, waist, or chest-mounted device. Device 700 could also take the form of a device that is not configured to be mounted to a body. For example, device 700 could take the form of a cell phone, control pendant, communications bridge, or other device. Device 700 also could take other forms.

In particular, FIG. 7 shows an example of a device 700 having a data collection system 710 that includes two sensors 712, 714, a user interface 720, communication interface 730 for communicating with another system (e.g., one or more other body-mountable devices, a cell phone or other controller device), and a controller 710. The components of the device 700 may be disposed on a mount or on some other structure for mounting the device to enable stable detection of one or more properties (e.g., velocity, acceleration, force) of a body segment of a user of the device 700, for example, mounting to an external body surface where one or more portions of subsurface vasculature or other anatomical elements are readily observable.

Controller 710 may be provided as a computing device that includes one or more processors 740. The one or more processors 740 can be configured to execute computer-readable program instructions 770 that are stored in the computer readable data storage 760. The program instructions 770 are executable by the one or more processors 740 to provide the functionality of a device 700 described herein, including any of the methods described herein.

The computer readable medium 760 may include or take the form of one or more non-transitory, computer-readable storage media that can be read or accessed by at least one processor 740. The one or more computer-readable storage media can include volatile and/or non-volatile storage components, such as optical, magnetic, organic or other memory or disc storage, which can be integrated in whole or in part with at least one of the one or more processors 740. In some embodiments, the computer readable medium 760 can be implemented using a single physical device (e.g., one optical, magnetic, organic or other memory or disc storage unit), while in other embodiments, the computer readable medium 760 can be implemented using two or more physical devices.

Sensors 712, 714 could include any components configured to detect properties and/or some other information about motor activity of a person and/or the performance of a prompted motor task by such a person as described elsewhere herein. The sensors 712, 714 could include accelerometers, gyroscopes, strain gauges, ambient light sensors, microphones, components of a touch screen (e.g., touch sensors, pressure sensors, capacitance sensors, impedance sensors), GPS receivers, temperature sensors, energy sensors, electromagnetic sensors, light sensors, chemical sensors, acoustical sensors, infrared sensors, ultraviolet sensors, tonometers, electrocardiogram electrodes, tissue impedance electrodes, or other types of sensors. The sensors 712, 714 could include photodetectors (e.g., light detectors, color detectors, polarity detectors, infrared detectors, ultraviolet detectors, cameras).

In some examples, one or more of the sensors 712, 714 could include energy emitters (e.g., light emitters, heaters, acoustical transducers, current sources, voltage sources) configured to enable detection of some property of a body of a person (e.g., of a portion of subsurface vasculature of the person) by illuminating, heating, injecting a current into, applying a voltage to, or otherwise introducing an energy to the one or more portions of the body of the person. For example, the sensors 712, 714 could include one or more Doppler ultrasonography probes. In some examples, the sensors 712, 714 could include active optical sensors configured to illuminate a portion of subsurface vasculature and/or blood therein and the detect light responsively emitted from the portion of subsurface vasculature. Such sensors could include laser Doppler flowmeters, dynamic laser speckle sensors, photoplethysmographic sensors, fluorescence imagers, or some other active and/or passive optical sensors.

The program instructions 770 stored on the computer readable medium 760 may include instructions to perform any of the methods described herein (e.g., the methods described with reference to FIG. 8).

The program instructions 770 can also include instructions for operating a user interface 720. For example, program instructions 770 may include instructions for displaying data collected by the data collection system 710 and analyzed by the controller 710, or for displaying one or more alerts. Program instructions 770 may include instructions for displaying data related to a determined health state of a person. Program instructions 770 may include instructions for prompting a person to perform a diagnostic motor task and/or for displaying data related to such a motor task (e.g., an identity or target of the motor task, feedback related to performance of the motor task). Further, program instructions 770 may include instructions to execute certain functions based on inputs accepted by the user interface 720, such as inputs accepted by one or more buttons disposed on the user interface.

Communication interface 730 may also be operated by instructions within the program instructions 770, such as instructions for sending and/or receiving information via a wireless antenna, which may be disposed on or in the device 700. The communication interface 730 can optionally include one or more oscillators, mixers, frequency injectors, etc. to modulate and/or demodulate information on a carrier frequency to be transmitted and/or received by the antenna. In some examples, the device 700 is configured to indicate an output from the processor by modulating an impedance of the antenna in a manner that is perceivable by a remote server or other remote computing device.

The program instructions 770 may, in some examples, be stored in a computer-readable medium and executed by a processor located external to the device 700. For example, the device 700 could be configured to generate and/or receive sensor signals and then transmit the data to a remote server, which may include a mobile device, a personal computer, the cloud, or any other remote system, for further processing.

The computer readable medium 760 may further contain other data or information, such as a baseline activity profile related to the person's motor activity or a medical and health history of a person, that may be useful in determining whether to prompt a person to perform a diagnostic motor task, whether a medical condition or some other specified condition is indicated, or to determine some other information. Further, the computer readable medium 760 may contain data corresponding to certain motor activity and/or physiological parameter baselines, above or below which some action may be performed (e.g., to prompt a person to perform a diagnostic motor task, to indicate that the person has a medical condition). The baselines may be pre-stored on the computer readable medium 760, may be transmitted from a remote source, such as a remote server, or may be generated by the device 700 itself. The program instructions 770 may include instructions for generating individual baselines (e.g., baseline activity profiles) for the person based on data collected over a certain number of measurement periods. Baselines may also be generated by a remote server and transmitted to the device 700 via communication interface 730. The program instructions 770 may also, upon determining that a medical or other condition is indicated, generate one or more recommendations for the person (e.g., a prompt to perform a diagnostic motor task). Such recommendations may alternatively be generated by the remote server and transmitted to the device 700.

In some examples, the collected baseline activity profiles, determined health state information, and generated recommendations and clinical protocols may additionally be input to a cloud network and be made available for download by a person's physician. Trend and other analyses may also be performed on the collected data, such as health state information, in the cloud computing network and be made available for download by physicians or clinicians.

Further, health state data from individuals or populations of individuals may be used by physicians or clinicians in monitoring efficacy of a drug or other treatment. For example, high-density, real-time data may be collected from a population of individuals who are participating in a clinical study to assess the safety and efficacy of a developmental drug or therapy. Such data may also be used on an individual level to assess a particular individual's response to a drug or therapy. Based on this data, a physician or clinician may be able to tailor a drug treatment to suit an individual's needs.

VII. EXAMPLE METHODS

Figure 8:
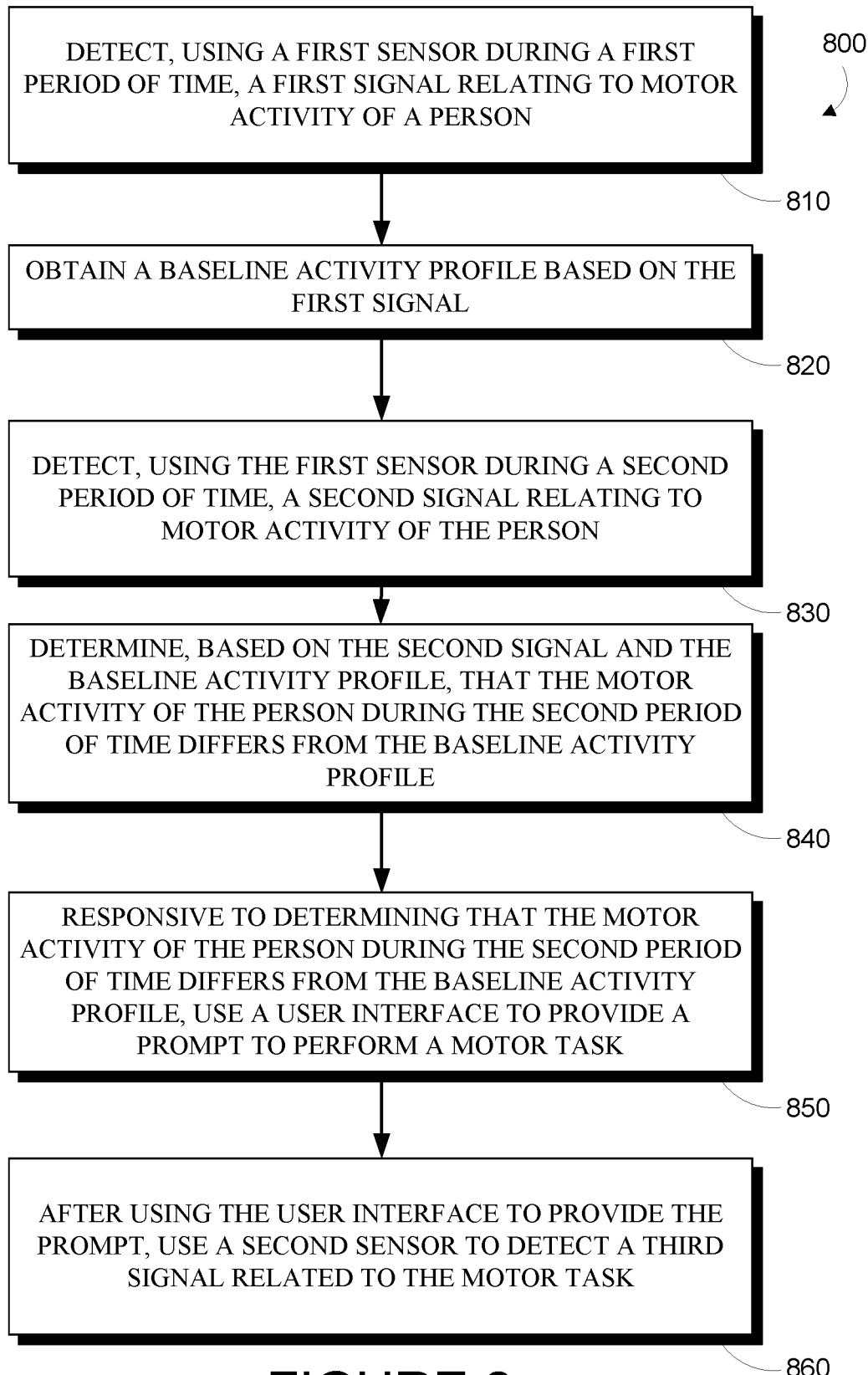
FIG. 8 is a flowchart of an example method.

FIG. 8 is a flowchart of a method 800. The method 800 could be performed by a controller of a system as described herein. Such a controller could be disposed in a body-mountable device, a cell phone, or some other device. Such a controller could include one or more processors that could execute instructions stored in a computer readable medium, where the instructions could cause the one or more processors to perform the method 800 when executed by the one or more processors.

The method 800 includes detecting, using a first sensor during a first period of time, a first signal relating to motor activity of a person (810). This could include receiving, via a wireless receiver, a wireless indication of the first signal from another device (e.g., a body-mountable device) that includes the first sensor. Alternatively, the controller and the first sensor could be disposed within the same device (e.g., a cell phone, a wrist-mountable or otherwise body-mountable device) and receiving the first signal (810) could include receiving the first signal via a wire, cable, trace, optical fiber, of other signal-conducting means of the device. Receiving the first signal (810) could include powering up and/or instructing the first sensor to operate to generate the first signal.

The method 800 further includes obtaining a baseline activity profile based on the first signal (820). This could include receiving, from a remote system (e.g., a server, a cloud computing service), an indication of the baseline activity profile. In such an example, the remote system could determine the baseline activity profile based on information transmitted from the controller, e.g., indications of the first signal transmitted from the controller. Additionally or alternatively, the controller could determine the baseline activity profile based on the first signal, e.g., based on a record of the first signal stored in a memory that is accessible by controller. The controller determining the baseline activity profile could include determining a sleep activity, a rest activity, an exercise activity, a locomotion activity, a specified diagnostic activity, a cooking activity, or some other activity. Determining the particular activity could include performing some filtering, transformation, thresholding, pattern matching, or other processes on the first signal. The controller determining the baseline activity profile could include determining, based on the first signal, one or more properties of motor activity of the person during the first period of time. For example, the controller could determine a percent of the first time period that the person was engaged in one or more activities (e.g., locomotion), a length or duration of one or more steps taken by the person, or some other property of the motor activity and/or of events within the motor activity.

The method 800 further includes detecting, using the first sensor during a second period of time, a second signal relating to motor activity of the person (830). The method 800 additionally includes determining, based on the second signal, that the motor activity of the person during the second period of time differs from the baseline activity profile (840). This could include determining, based on the second signal, one or more properties of motor activity of the person during the second period of time. For example, the controller could determine a percent of the first time period that the person was engaged in one or more activities (e.g., locomotion), a length or duration of one or more steps taken by the person, or some other property of the motor activity and/or of events within the motor activity. Determining that the motor activity of the person during the second period of time differs from the baseline activity profile could include comparing a determined property of the motor activity during the second period of time to a threshold (e.g., a threshold that is part of and/or determined from the baseline activity profile), performing pattern matching on the second signal (e.g., comparing a pattern of ankle motion during locomotion detected during the second period of time to a pattern of ankle motion during locomotion represented by the baseline activity profile), or performing some other determination.

In some examples, the first period of time and the second period of time could be non-overlapping. Alternatively, the first period of time and the second period of time could be wholly or partially overlapping. For example, the second period of time could be a portion of the first period of time (e.g., a terminal portion of the first period of time). In such an example, the baseline activity profile could be determined, in part, based on the signals detected during the second period of time.

The method 800 further includes, responsive to determining that the motor activity of the person during the second period of time differs from the baseline activity profile, using a user interface to provide a prompt to perform a motor task (850). This could include emitting a sound, operating a vibrator, emitting a light, operating a display, or providing by some other means an indication that can be perceived by a person such that the person is prompted to perform the motor task. Providing a prompt to perform a motor task could include indicating some information related to performance of the motor task, e.g., indicating an identity of the motor task within an enumerated list of different possible motor tasks, indicating a timing of the motor task (e.g., indicating when the person should begin to perform the motor task), indicating a target of the motor task (e.g., indicating a particular icon or button that the person should touch, press, or otherwise interact with as part of performing the motor task), or indicating some other information.

The method 800 further includes, after using the user interface to provide the prompt, using a second sensor to detect a third signal related to the motor task (860). This could include detecting a force, an acceleration, a rotation, or some other property related to a particular body segment of a person's body, e.g., to detect motion of the person's foot or ankle during locomotion. In another example, the third signal could be an output of a button, a keyboard, a touchscreen, a mouse, or some other element of a user interface. Detecting the third signal could include receiving, via a wireless receiver or other communications element, a wired or wireless indication of the third signal from another device (e.g., a body-mountable device, a keyboard or other user interface element, a clinical assessment apparatus) that includes the second sensor.

The method 800 could include additional or alternative steps. In some examples, the method 800 could include determining a health state or other information about the person based on based on the third signal and/or based on some other signals. In some examples, the method 800 could include providing, to a user (e.g., to the person), an indication of such a determined health state or other information. The method 800 could include transmitting indications of the third signal, second signal, first signal, and/or some other signals to a remote system (e.g., a server, a cloud computing service) and receiving, from the remote system, a determined health state or other information about the person determined, based on the transmitted signals, by the remote system.

The example method 800 illustrated in FIG. 8 is meant as an illustrative, non-limiting example. Additional or alternative elements of the method and additional or alternative components of a related system (e.g., a system of wearable devices) are anticipated, as will be obvious to one skilled in the art.

VIII. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
   A body-mountable device mountable to a body segment of a person;
   a first sensor, wherein the body-mountable device comprises the first sensor, and wherein the first sensor monitors motion of the body segment of the person;
   a second sensor that monitors performance of a motor task;
   a user interface, wherein the body-mountable device comprises the user interface; and
   a controller communicatively coupled to the first sensor, the second sensor, and the user interface, wherein the controller comprises one or more processors programmed to perform operations comprising:
   detecting, by a first processor of the one or more processors using the first sensor during a first period of time, a first signal relating to motor activity of the person, wherein the body-mountable device comprises the first processor;

obtaining a baseline activity profile based on the first signal;

detecting, by the first processor using the first sensor during a second period of time, a second signal relating to motor activity of the person;

determining, by the first processor based on the second signal and the baseline activity profile, that the motor activity of the person during the second period of time differs from the baseline activity profile; and responsive to determining that the motor activity of the person during the second period of time differs from the baseline activity profile:

providing, by the first processor operating the user interface, a prompt to perform a motor task, wherein the motor task includes motion of one or more body parts associated with at least one of walking, standing, sitting, typing a phrase, generating a sound, touching one finger to another finger, or an assessment task that is part of a clinical diagnostic battery;

transmitting, by the first processor, a command that activates the second sensor to measure one or more properties of the motion of the one or more body parts related to performing the motor task and to output a third signal based on measurement of the one or more properties; and detecting the third signal, wherein the third signal indicates a degree of progression of a disease state of the person.

2. The system of claim 1, wherein the operations further comprise:

determining, based on the second signal, a particular activity of the person during the second period of time;

determining, based on the second signal, that one or more discrete events relating to the particular activity occurred during the second period of time; and determining, based on the second signal, a characteristic of each of the one or more discrete events during the second period of time, wherein determining that the motor activity of the person during the second period of time differs from the baseline activity profile comprises determining that the set of determined characteristics of each of the one or more discrete events during the second period of time differs from the baseline activity profile.

3. The system of claim 1, further comprising a transceiver that is operably coupled to the controller, wherein the body-mountable device comprises the transceiver, and wherein obtaining the baseline activity profile comprises:

transmitting, using the transceiver, an indication of the first signal to a remote server; and receiving, using the transceiver, an indication of the baseline activity profile from the remote server.

4. The system of claim 3, wherein the operations further comprise:

transmitting, using the transceiver, an indication of the third signal to the remote server.

5. The system of claim 1, wherein the second sensor comprises at least one of an accelerometer or a gyroscope.

6. The system of claim 1, wherein the second sensor comprises a microphone.

7. A non-transitory computer-readable medium having stored thereon instructions executable by at least one processor of a body-mountable device to perform operations comprising:

detecting, using a first sensor of the body-mountable device during a first period of time, a first signal relating to motor activity of a person;

obtaining, from a remote server, a baseline activity profile based on the first signal;

detecting, using the first sensor during a second period of time, a second signal relating to motor activity of the person;

determining, based on the second signal and the baseline activity profile, that the motor activity of the person during the second period of time differs from the baseline activity profile; and responsive to determining that the motor activity of the person during the second period of time differs from the baseline activity profile:

operating a user interface of the body-mountable device to provide a prompt to perform a motor task, wherein the motor task includes motion of one or more body parts associated with at least one of walking, standing, sitting, typing a phrase, generating a sound, touching one finger to another finger, or an assessment task that is part of a clinical diagnostic battery;

transmitting a command that activates a second sensor to measure one or more properties of the motion of the one or more body parts related to performing the motor task and to output a third signal based on measurement of the one or more properties; and detecting the third signal, wherein the third signal indicates a degree of progression of a disease state of the person.

8. The non-transitory computer-readable medium of claim 7, wherein using the first sensor to detect the second signal comprises operating a receiver to receive a wireless signal related to the second signal.

9. The non-transitory computer-readable medium of claim 7, wherein the operations further comprise:

determining, based on the second signal, a particular activity of the person during the second period of time;

determining, based on the second signal, that one or more discrete events relating to the particular activity occurred during the second period of time; and determining, based on the second signal, a characteristic of each of the one or more discrete events during the second period of time, wherein determining that the motor activity of the person during the second period of time differs from the baseline activity profile comprises determining that the set of determined characteristics of each of the one or more discrete events during the second period of time differs from the baseline activity profile.

10. The non-transitory computer-readable medium of claim 9, wherein the second signal is related to motion of an ankle of a person, and wherein determining a characteristic of each of the one or more discrete events comprises determining a duration of each of one or more steps taken by the person.

11. The non-transitory computer-readable medium of claim 9, wherein the second signal is related to motion of a torso of a person, and wherein determining a characteristic of each of the one or more discrete events comprises determining a mean angular velocity of each of one or more turns taken by the person.

12. The non-transitory computer-readable medium of claim 7, wherein obtaining the baseline activity profile comprises determining the baseline activity profile based on the first signal.

13. The non-transitory computer-readable medium of claim 7, wherein obtaining the baseline activity profile comprises:
   operating a transceiver of the body-mountable device to transmit an indication of the first signal to a remote server; and
   operating the transceiver to receive an indication of the baseline activity profile from the remote server.

14. The non-transitory computer-readable medium of claim 7, wherein the operations further comprise:
   operating a transceiver to transmit an indication of the third signal to a remote server.

15. The non-transitory computer-readable medium of claim 14, wherein the operations further comprise:
   operating the transceiver to receive health state information from the remote server; and
   operating the user interface to provide an indication of the received health state information.

16. The non-transitory computer-readable medium of claim 7, wherein the operations further comprise:
   determining, based on the third signal, a degree of progression of a movement disorder.

17. The non-transitory computer-readable medium of claim 7, wherein the second sensor comprises at least one of an accelerometer or a gyroscope.

18. The non-transitory computer-readable medium of claim 7, wherein the second sensor comprises a microphone.

19. The non-transitory computer-readable medium of claim 7, wherein the second sensor comprises a touch sensor of a touch screen.

\* \* \* \* \*